(12) United States Patent
Shrivastava et al.

(10) Patent No.: US 11,272,945 B2
(45) Date of Patent: Mar. 15, 2022

(54) DEVICE FOR REMOVING AN EMBOLUS

(71) Applicant: INNOVA VASCULAR, INC., Irvine, CA (US)

(72) Inventors: Sanjay Shrivastava, Irvine, CA (US); Jianlu Ma, Irvine, CA (US)

(73) Assignee: INNOVA VASCULAR, INC., Irvine, CA (US)

( * ) Notice: Subject to any disclaimer, the term of this patent is extended or adjusted under 35 U.S.C. 154(b) by 145 days.

(21) Appl. No.: 16/597,727

(22) Filed: Oct. 9, 2019

(65) Prior Publication Data

US 2020/0113588 A1    Apr. 16, 2020

Related U.S. Application Data

(60) Provisional application No. 62/744,107, filed on Oct. 10, 2018.

(51) Int. Cl.
*A61B 17/221* (2006.01)
*A61M 25/00* (2006.01)
(Continued)

(52) U.S. Cl.
CPC .. *A61B 17/221* (2013.01); *A61B 2017/00867* (2013.01); *A61B 2017/2212* (2013.01);
(Continued)

(58) Field of Classification Search
CPC ........ A61B 17/221; A61B 2017/00867; A61B 2017/22038; A61B 2017/2212;
(Continued)

(56) References Cited

U.S. PATENT DOCUMENTS

| | | | |
|---|---|---|---|
| 5,370,623 | A | 12/1994 | Kreamer |
| 5,441,483 | A | 8/1995 | Avitall |

(Continued)

FOREIGN PATENT DOCUMENTS

| | | |
|---|---|---|
| AU | 2005200491 A1 | 3/2005 |
| EP | 1695673 A2 | 8/2006 |

(Continued)

OTHER PUBLICATIONS

Gillian Pearce, Rev.Neil, D.Perkinson, Julianong, Matthew Burley, Julian Spence, Paul Brookfield, David Murcott, The "GP" Mechanical Thrombectomy Device, Journal of Stroke and Cerebrovascular Diseases, Jul.-Aug. 2009, pp. 288-293, National Stroke Association, Published by Elsevier Inc. https://www.sciencedirect.com/science/article/abs/pii/S105230570800270X.

(Continued)

*Primary Examiner* — Mohamed G Gabr
(74) *Attorney, Agent, or Firm* — Mahesh Law Group PC; Kumar Maheshwari

(57) ABSTRACT

A clot retrieval device is provided. The clot retrieval device includes a capturing basket having an opening at a proximal end where the capturing basket is deployable downstream from a clot in a blood vessel. The capturing basket is configured to surround a portion of the clot and the opening in the proximal end of the capturing basket is configured to reduce in size such that the capturing basket conforms around the portion of the clot and be retrieved after the capturing basket conforms around the portion of the clot.

12 Claims, 18 Drawing Sheets

(51) Int. Cl.
*A61M 25/01* (2006.01)
*A61B 17/00* (2006.01)

(52) U.S. Cl.
CPC ..... *A61M 25/0015* (2013.01); *A61M 25/0082* (2013.01); *A61M 25/0108* (2013.01)

(58) Field of Classification Search
CPC .......... A61B 2017/320775; A61M 2025/1052; A61M 2025/1093; A61M 2025/1097; A61M 25/0015; A61M 25/0074; A61M 25/0082; A61M 25/0108; A61M 25/1002
See application file for complete search history.

(56) References Cited

U.S. PATENT DOCUMENTS

| | | | |
|---|---|---|---|
| 6,142,987 A | 11/2000 | Tsugita | |
| 6,168,579 B1 | 1/2001 | Tsugita | |
| 6,251,122 B1 | 6/2001 | Tsukernik | |
| 6,277,139 B1 | 8/2001 | Levinson et al. | |
| 6,652,554 B1 | 11/2003 | Wholey et al. | |
| 6,676,683 B1 | 1/2004 | Addis | |
| 7,232,453 B2 | 6/2007 | Shimon | |
| 7,479,153 B2 | 1/2009 | Belef | |
| 7,963,989 B2 | 6/2011 | McEwan | |
| 8,152,831 B2 | 4/2012 | Magnuson et al. | |
| 8,454,649 B2 | 6/2013 | Cragg et al. | |
| 9,044,305 B2 | 6/2015 | Grewe | |
| 9,358,022 B2 | 6/2016 | Morsi | |
| 9,445,829 B2 | 9/2016 | Brady et al. | |
| 9,642,635 B2 | 5/2017 | Vale et al. | |
| 9,642,639 B2 | 5/2017 | Brady et al. | |
| 9,668,849 B2 | 6/2017 | Shimon | |
| 9,700,331 B2 | 7/2017 | Grandfield et al. | |
| 9,717,519 B2 | 8/2017 | Rosenbluth et al. | |
| 9,848,881 B2 | 12/2017 | Sutton et al. | |
| 9,901,245 B2 | 2/2018 | Kovarik et al. | |
| 9,943,321 B2 | 4/2018 | Nita | |
| 9,943,323 B2 | 4/2018 | Martin et al. | |
| 9,999,493 B2 | 6/2018 | Nguyen et al. | |
| 10,004,531 B2 | 6/2018 | Rosenbluth et al. | |
| 10,034,680 B2 | 7/2018 | Brady et al. | |
| 10,045,790 B2 | 8/2018 | Cox et al. | |
| 2002/0123766 A1 | 9/2002 | Seguin et al. | |
| 2003/0065356 A1 | 4/2003 | Tsugita et al. | |
| 2004/0162576 A1 | 8/2004 | Barbut et al. | |
| 2005/0033347 A1 | 2/2005 | Rauker et al. | |
| 2005/0228417 A1 | 10/2005 | Teitelbaum et al. | |
| 2006/0020286 A1 | 1/2006 | Niermann | |
| 2006/0229660 A1* | 10/2006 | Pal | A61F 2/013 606/200 |
| 2006/0276805 A1 | 12/2006 | Yu | |
| 2007/0005103 A1 | 1/2007 | Schaeffer | |
| 2008/0103522 A1 | 5/2008 | Steingisser et al. | |
| 2011/0202088 A1 | 8/2011 | Eckhouse et al. | |
| 2014/0074144 A1* | 3/2014 | Shrivastava | A61M 39/06 606/200 |
| 2014/0371781 A1 | 12/2014 | Morgan | |
| 2017/0112514 A1* | 4/2017 | Marchand | A61B 17/3415 |
| 2018/0132874 A1 | 5/2018 | Ulm, III | |
| 2018/0221128 A1 | 8/2018 | Shishehbor et al. | |
| 2019/0223995 A1 | 7/2019 | Besselink | |

FOREIGN PATENT DOCUMENTS

| | | |
|---|---|---|
| WO | 2001045590 A2 | 6/2001 |
| WO | 2009031338 A1 | 3/2009 |

OTHER PUBLICATIONS

Melhem J.A.Sharafuddin, Marshall E.Hicks, Current Status of Percutaneous Mechanical Thrombectomy. Part II. Devices and Mechanisms of Action, Journal of Vascular and Interventional Radiology, Jan. 1998, pp. 15-31, vol. 9, Issue 1, Society of Interventional Radiology, Published by Elsevier Inc. https://www.sciencedirect.com/science/article/pii/S1051044398704774.

Tamara Bhandari, Costly blood clot procedure may not be worth the risk, futurity, Dec. 8, 2017, Washington University in St. Louis. https://www.futurity.org/deep-vein-thrombosis-1626192/.

* cited by examiner

DEVICE FOR REMOVING AN EMBOLUS

PRIORITY CLAIM TO RELATED APPLICATIONS

This application claims the benefit of U.S. Provisional Application No. 62/744,107 filed Oct. 10, 2018 entitled as "An Apparatus and Method for Removing Large Clots for Treating Pulmonary Embolism", which is incorporated herein by reference in its entirety.

FIELD OF THE INVENTION

This disclosure relates to the field of medical devices that remove emboli.

BACKGROUND

Pulmonary embolism (PE) is a condition resulting from emboli or thombi getting lodged in one or more of the pulmonary arteries. The presence of a pulmonary embolus can cut off blood to large portions of the lungs and be potentially fatal. Emboli are particularly difficult to remove because they are often large in size and need to traverse a complex and tortuous pathway to be extracted out of the body using an endovascular approach. Pulmonary embolism can cause right heart strain resulting in heart failure leading to death in many cases. PE results in more than 100,000 deaths in the US each year. One approach to treat PE is by removing the clot present in pulmonary arteries outside the body. There is a need for a method and device that safely removes embolic mass from pulmonary arteries.

SUMMARY

The present disclosure includes a device and a process for retrieving a clot in PE patients. The device includes a capturing basket having an opening at a proximal end where the capturing basket is deployable downstream from a clot in a blood vessel. The capturing basket is configured to surround a portion of the clot and the opening in the proximal end of the capturing basket is configured to reduce in size such that the capturing basket conforms around the portion of the clot and be retrieved after the capturing basket conforms around the portion of the clot. The capturing basket may further include spaced pores that increase in size from a distal end of the capturing basket to the proximal end of the capturing basket. The capturing basket may be made of braided wire and the spaced pores are formed from spaces between the braided wire. The braided wire may be Nitinol. The capturing basket may further include radiopaque markers that are positioned to reveal the clot under fluoroscopy when the capturing basket conforms to the portion of the clot. The capturing basket may be configured to be delivered by a delivery catheter from an upstream direction in the blood vessel where a distal opening of the delivery catheter has one or more extrusions extending from an inner surface of the delivery catheter and one or more extrusions have sharp edges. The capturing basket may be configured to be delivered by a delivery catheter from an upstream direction in the blood vessel prior to being retrieved by the delivery catheter where the distal opening of the delivery catheter is configured to increase in size to retrieve the capturing basket. The distal end of the capturing basket may be made of a soft material such that the distal end of the capturing basket is deformable upon contact with an interior wall of the blood vessel.

In an exemplary embodiment, a clot retrieval device includes a capturing basket having an opening at a proximal end and a delivery catheter configured to deliver the capturing basket where the capturing basket comprises braided wire that has spaced pores that increase in size from a distal end of the capturing basket to the proximal end of the capturing basket. The capturing basket is configured to surround a portion of the clot and the opening in the proximal end of the capturing basket is configured to reduce in size such that the capturing basket conforms around the portion of the clot and the opening in the proximal end is further configured to shear the clot when the opening in the proximal end is reduced in size. The proximal end may be further configured to increase in size and be configured to shear clot pieces away from the clot by repeatedly reducing in size and increasing in size. The capturing basket of the clot retrieval device may include radiopaque markers that are positioned to reveal the clot under fluoroscopy when the capturing basket conforms to the portion of the clot where the radiopaque markers have a textured surface. The radiopaque markers with the textured surface may be positioned within the capturing basket to capture the clot pieces that shear away from the clot. The opening in the proximal end may be reduced in size by a closing mechanism where the closing mechanism comprises a wire that is woven around the opening in the proximal end and one end of the wire is coupled to a delivery wire that effects the delivery and retrieval of the capturing basket. The closing mechanism may have a locking mechanism that, when enabled, prevents the opening in the proximal end from reducing in size.

Also in an exemplary embodiment, a clot retrieval device includes a capturing basket having an opening at a proximal end and a delivery catheter configured to deliver the capturing basket from a distal end of the delivery catheter where the capturing basket has spaced pores formed from spaces between a braided wire that increase in size from a distal end of the capturing basket to the proximal end of the capturing basket. The capturing basket is configured to surround a portion of the clot and the opening in the proximal end of the capturing basket is configured to reduce in size such that the capturing basket conforms around the portion of the clot and be retrieved by the distal opening of the delivery catheter after the capturing basket conforms around the portion of the clot. The distal opening of the delivery catheter may have one or more extrusions extending from an inner surface of the delivery catheter where the one or more extrusions have sharp edges and the one or more extrusions are retractable and the one or more extrusions with sharp edges are configured to shear the clot as the capturing basket is retrieved by the distal end of the delivery catheter. The delivery catheter may have one or more slits at the distal opening of the delivery catheter where the distal opening of the delivery catheter is configured to increase in size to retrieve the capturing basket. The clot retrieval device may further include a balloon catheter located near the distal opening of the delivery catheter that has a funnel shape when inflated. The balloon catheter may have pores that, when the balloon catheter is inflated, allow blood to flow through the balloon catheter and prevent large blood clots from flowing through the balloon catheter. The proximal end of the delivery catheter may be configured to be aspirated to aid in the retrieval of the capturing basket into the distal end of the delivery catheter.

DETAILED DESCRIPTION

Figure 1:
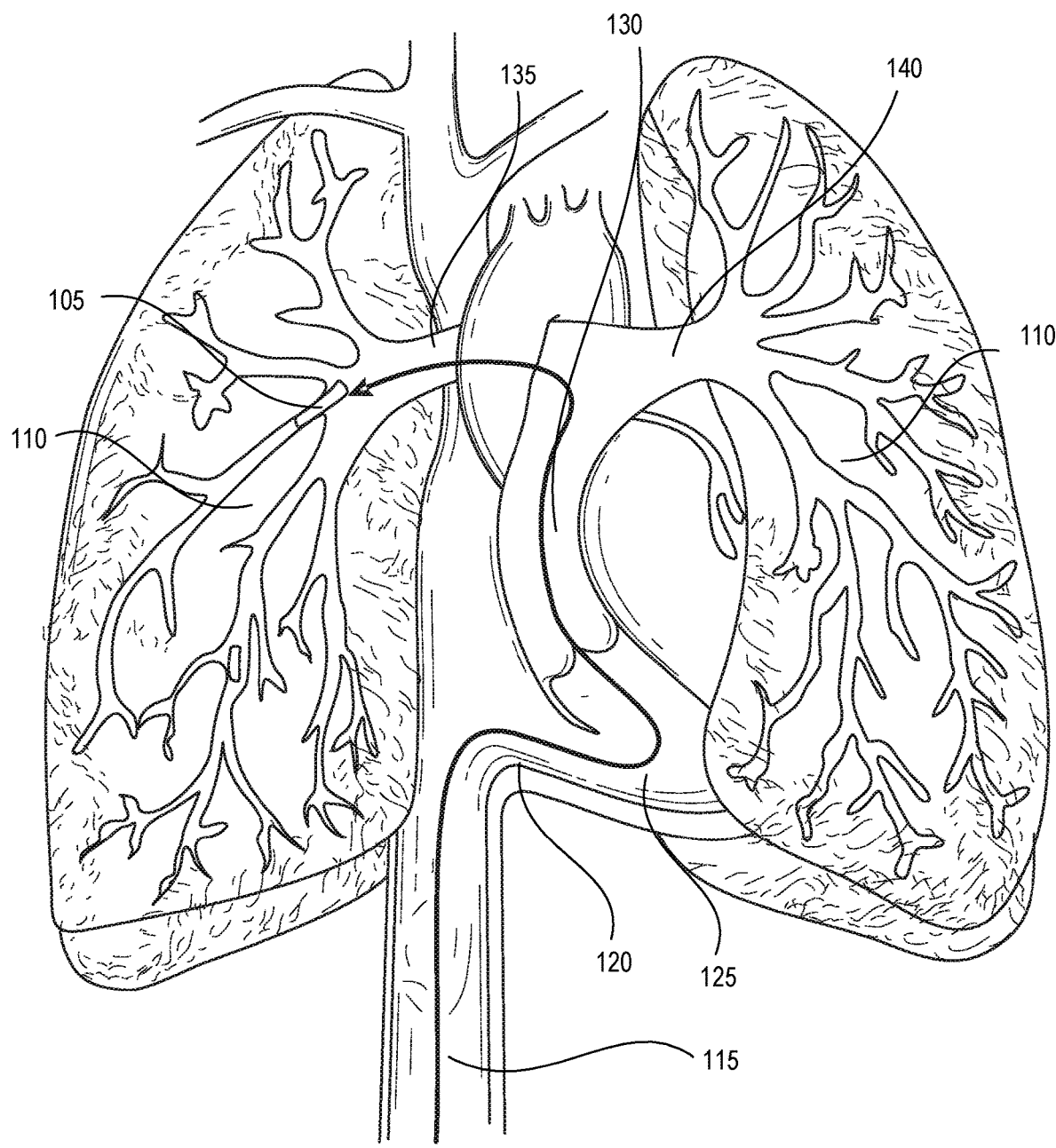
FIG. 1 illustrates a vasculature, within which an embolus that is blocking a blood vessel may be retrieved.

The disclosed subject matter is an apparatus for trapping and retrieving an embolus. The apparatus comprises a capturing basket with a small pore conical structure at a distal end. The distal end of the capturing basket is coupled to a mid-region that is cylindrical. The mid region of the capturing basket is coupled to a proximal end that is cylindrical and has a larger pore size than the distal end. The capturing basket is attached to a pusher-wire, which is a wire that delivers the capturing basket through a vasculature to the location of an embolus and pushes the capturing basket across an embolus via a catheter. The catheter may deploy the capturing basket once the catheter crosses the distal end of the embolus. The catheter may include a balloon that, when inflated, increases the opening of the distal end of the catheter. The balloon may have a funnel shape, which facilitates retrieval of the capturing basket into the catheter after the capturing basket traps an embolus. The balloon may further include a grid structure where the open areas of balloon allow blood to pass through the balloon when the balloon is inflated. In various embodiments, the balloon is not limited to a funnel shape. The balloon may be various shapes such as a disc or a cylinder. External aspiration may be used on the apparatus to aid in retrieving an embolus.

The capturing basket with pores surrounds and captures emboli inside the capturing basket. The pusher-wire may be used to pull the capturing basket around the embolus after the capturing basket has been deployed. The capturing basket may have a gradient in pore size, whereby smaller pores are at the distal end of the capturing basket and larger pores are at the proximal end of the capturing basket. The distal end of the capturing basket may be made using a micro-braid while the proximal end of the capturing basket may be made by laser cutting and shape setting a tube. The micro-braided distal end may be connected to the laser cut proximal end via an interwoven braided process and/or using a laser welding process. Alternatively, the proximal end may be made by continuing the micro-braid with a large pore braid. Also alternatively, the whole capturing basket may be made by laser cutting and shape setting tubing. In various embodiments, the capturing basket is made by layered deposition using 3D printing. Also, in various embodiments, vapor deposition can be employed to make the capturing basket. In one embodiment, the capturing basket has a diameter of 3-30 mm and a length of 10-300 mm when deployed.

The braiding may be done using fully radiopaque wire such as platinum. Alternatively, the braiding may be done using partially radiopaque wire such as drawn-forged ("DF") Nitinol wire. Non-radiopaque wire, such as Nitinol, titanium, Co—Cr alloy, a polymer, or combination of any of the aforementioned materials may also be used to perform the braiding. A heat-treatment process may be used to shape-set the braided structure into its final shape. For enhanced radiopacity and visualization, radiopaque markers made of tantalum, platinum, or other radiopaque materials may be installed into various portions of the capturing basket.

A pull-string mechanism may be used to close the proximal end of the capturing basket. When employed, the pull-string mechanism may fully or partially close the proximal end of the capturing basket when the capturing basket surrounds an embolus. The pull-string mechanism thus prevents the surrounded embolus from leaving the capturing basket. Once the pull-string mechanism is employed, the capturing basket, with embolus inside, may be retrieved into a catheter or balloon catheter without danger of the embolus escaping. The pull-string mechanism may be made by weaving wire into the proximal end of the capturing basket. An additional locking mechanism may be used to keep the proximal end of the capturing basket open or closed during a treatment process.

The pore size gradient in the capturing basket acts as a secondary embolus capture device. Pieces that dislodge off the embolus, that was surrounded by the capturing basket, may be trapped in the distal end of the capturing basket. For enhanced clot retention, the surface of the wire or tubing that makes up the capturing basket may be textured, which imparts roughness to the surface. The roughness helps retain an embolus and keeps the embolus trapped in the braided structure in all portions of the capturing basket. The textured surface may be prepared using laser or other means. Radiopaque markers may be textured to impart additional embolus retention. The textured radiopaque markers may be located in multiple radial directions around the capturing basket to retain dislodged pieces of embolus in any portion of the capturing basket.

Pieces of dislodged embolus may be sheared intentionally in various ways. In addition to preventing an embolus from leaving the capturing basket, the pull-string mechanism may be used to shear an embolus to facilitate the retrieval of the embolus. In order to remove large emboli, it can be helpful to shear the large emboli into smaller pieces without losing control of the smaller pieces. Shearing the embolus with the pull-string mechanism of the capturing basket effectively controls the smaller pieces of the embolus that are sheared off because the smaller pieces fall into the capturing basket. Shearing an embolus may be accomplished by repeated activation of the pull-string mechanism to open and close the proximal end of the capturing basket.

Embolus pieces may be sheared through the action of pulling an embolus that is trapped within a capturing basket into the catheter. The distal opening of the catheter may break an embolus as the embolus is forced into an opening that is smaller than the cross-section of the embolus. The embolus may be repeated forced into the catheter and extruded out of the catheter to break up the embolus. Repeated extrusion actions may break up the embolus into ever smaller pieces that could be retrieved by a lower profile catheter. Repeated In addition to breaking the embolus by forcing the embolus through the distal opening of the catheter, an inner lumen of the catheter may have sharp edges that slice the embolus as the embolus is pulled into the catheter. The sharp edges may be activated while an embolus is captive within the catheter. The activation may be accomplished by pushing the sharp edge using a pusherwire that is separate from the pusherwire that is connected to the capturing basket. In an exemplary embodiment, the distal opening of the catheter is expandable to allow easy retrieval of the capturing basket that has trapped an embolus. The expandable distal opening may have slits, which allow the opening to be expanded.

In one embodiment, aspiration of the proximal end of the catheter may be used to increase the efficiency of embolus removal. The aspiration may be performed while the embolus is trapped within the capturing basket and being pulled into the catheter. In various embodiments, aspiration is not used to retrieve emboli.

A balloon catheter located at the distal tip of the catheter may be used to improve retrieval of the capturing basket and minimize the number pieces that break away freely from the embolus. When inflated, the balloon catheter can have a funnel shaped grid or pores. The funnel directs the capturing basket into the catheter while the grid of pores allows blood to flow through the balloon catheter. The balloon catheter may have various shapes other than a funnel such as a disc or a cylinder.

Referring to FIG. 1, FIG. 1 is an illustration of a vasculature 100 where an embolus 105 can get clogged. A common type of medical condition is a pulmonary embolism, where an embolus gets trapped in the pulmonary artery 130. Most emboli form within veins deep in the body, such as in the legs.

The formed embolus 105 may travel from the legs through the inferior vena cava 115 to the right atrium 120 and right ventricle 125 of the heart. The embolus may travel from the right ventricle 125 to the pulmonary artery 130. The pulmonary artery 130 bifurcates into a right pulmonary artery 135 and a left pulmonary artery 140. The right pulmonary artery 135 and left pulmonary artery 140 continually bifurcate further into the lungs 110 to oxygenate the blood. As the right pulmonary artery 135 and left pulmonary artery branch, they become continually smaller, such that the embolus 105 travelling through them may become stuck or lodged and inhibit or reduce blood flow downstream for the ebmolus.

The act of an embolus getting caught in the pulmonary artery, called a pulmonary embolism, reduces or cuts off the flow of blood to a part of the lungs 110. A pulmonary embolism is a serious condition that damages the lungs 110 and reduces the oxygen content in the blood. The disclosed subject matter is an apparatus that is pushed through the pulmonary artery 130 and delivered to the site of the embolus 105. The apparatus may trap the embolus 105 so the embolus 105 can be retrieved from the body.

Figure 2:
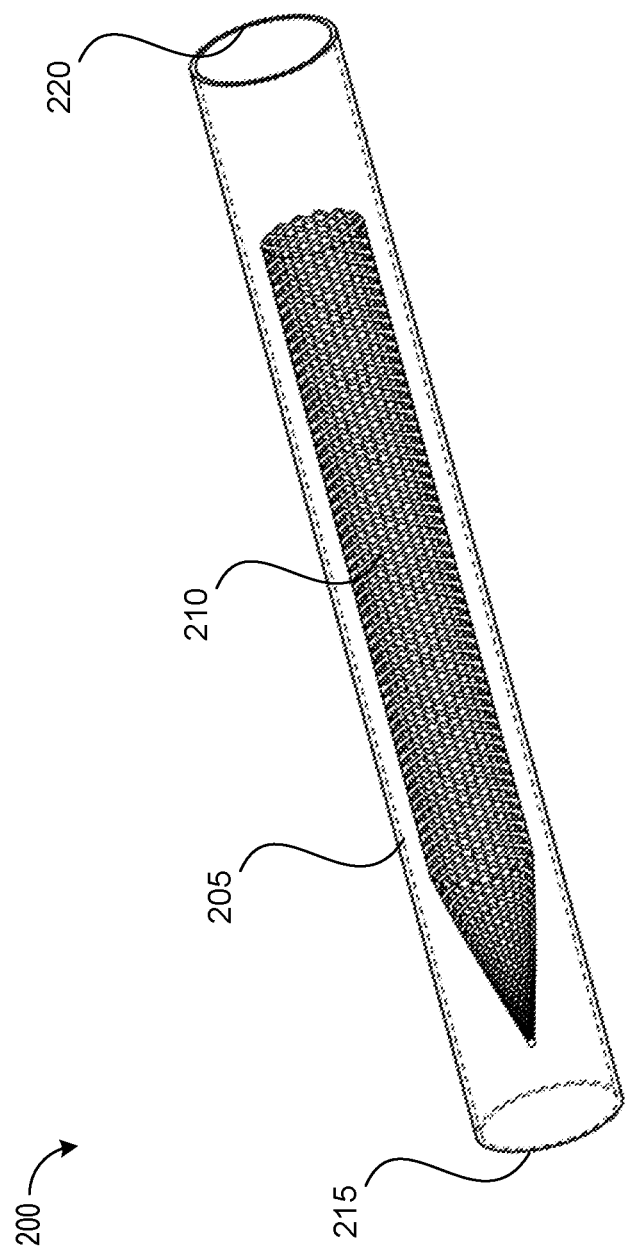
FIG. 2 illustrates an example of an apparatus for retrieving an embolus.

Referring to FIG. 2, FIG. 2 is an illustration of the apparatus 200 for trapping and retrieving an embolus 105. The apparatus 200 includes a catheter 205 and a capturing basket 210. The capturing basket 210 may be expandable and made of braided metal wire. The catheter 205 has an opening at a distal end 215 and a proximal end 220. The catheter 205 may be guided to an embolus 105 through a vasculature by a pushwire. When the catheter 205, with the capturing basket 210 inside the catheter, is guided to the embolus 105, the capturing basket 210 may be pushed out of the distal end 215 of the catheter 205.

In various embodiments, the capturing basket 210 may be configured to expand once the capturing basket 210 is pushed out of the catheter 205. The capturing basket 210, which is expandable, may be made of a material, such as Nitinol, that remains deformed at cold temperatures and expands at body temperature to a preset shape. The capturing basket 210 may be shaped to fill the inside of a blood vessel when the capturing basket 210 is expanded.

In addition to delivery the capturing basket 210 to an embolus 105, the catheter 205 may also be configured to retrieve a capturing basket 210 after the capturing basket 210 has trapped an embolus 105. The capturing basket 210 may be pushed out of the catheter 205 and retrieved by the catheter 205 at the distal end 215 of the catheter 205. In various embodiments, the proximal end 220 of the catheter 205 may be configured to be aspirated to aid in retrieving the capturing basket 210.

Figure 3A:
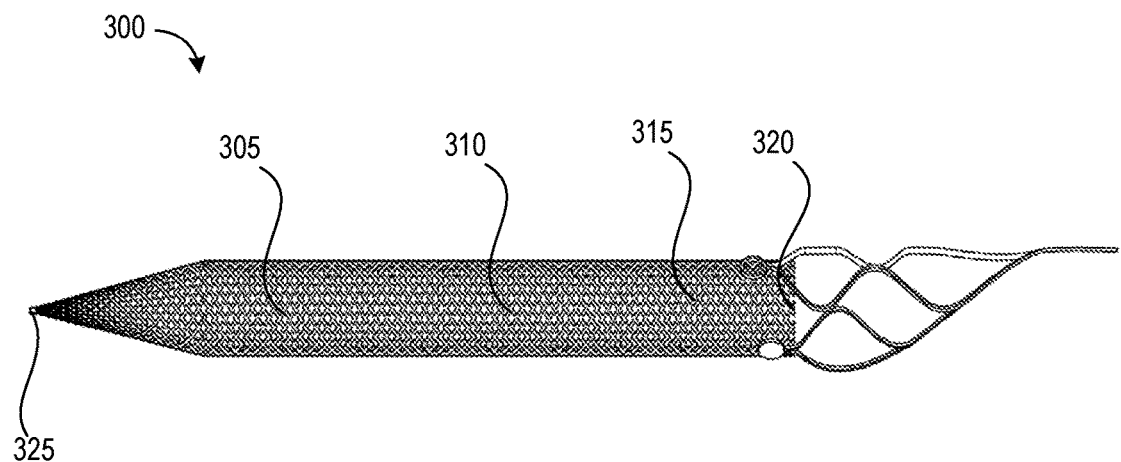
FIG. 3A illustrates an example of a capturing basket.

Referring to FIG. 3A, FIG. 3A illustrates an embodiment of the capturing basket 300 after the capturing basket 300 has been deployed from the catheter. The capturing basket 300 has a cone shaped distal-portion 305, a cylinder shaped mid-portion 310, and a cylinder shaped proximal-portion 315. Various embodiments may have different shapes for the distal-portion 305, mid-portion 310, and proximal-portion 315. The end of the proximal-portion 315 is a proximal opening 320 where the embolus 105 enters the capturing basket 300. In various embodiments, the tip 325 of the distal-portion 305 is made of soft metal that is configured to deform, rather than pierce, as it makes contact with the lumen of a blood vessel. In various embodiments, the capturing basket 300 has a diameter that ranges from 3-30 mm and a length that ranges from 10-300 mm.

The capturing basket 300 has regularly spaced pores. The regularly spaced pores increase in size gradually from the distal-portion 305 to the proximal portion 315. The gradient of pores in the capturing basket 300 serves multiple purposes, including but not limited to: making the capturing basket 300 more deliverable in the body, making the capturing basket 300 more conformable to the embolus 105, and allowing the capturing basket 300 to trap pieces that break off of the embolus 105. The larger pores at the proximal portion 315 allow the capturing basket 300 to be packed and/or deformed into a small space as the capturing basket 300 is delivered in the catheter. The larger pores at the proximal portion 315 also increase the flexibility of the capturing basket 300, which allows the capturing basket 300 to more easily conform to the shape of the embolus 105. The ability to bend to the embolus 105 has many advantages. The capturing basket 300 may increase in diameter to conform to an embolus 105 that is larger in diameter than the capturing basket 300. Further, the changing silhouette of the capturing basket 300, as the capturing basket conforms to the shape of the embolus 105 under fluoroscopy, signals to a user that the embolus 105 is inside the capturing basket 300.

On the other hand, the smaller pores at the distal-portion 305 are small enough to capture tiny pieces that break from the embolus 105 as the embolus is trapped by the capturing basket 300. Pieces that break off of the embolus 105, and are not trapped, could become clogged in other blood vessels, which may be dangerous to a patient. The ability to capture small pieces allows for the embolus 105 to be safely broken up without creating additional danger to the patient. Intentionally breaking up emboli 105 that are too big to be retrieved is an option made possible by the smaller pores at the distal-portion 305. Both the capturing basket 300 and catheter may be employed to break up large emboli 105 and trap the pieces of the emboli 105 in the distal-portion 305.

The proximal opening 320 may be configured to reduce in size to trap the embolus 105 once the embolus 105 is inside the capturing basket 300. In one embodiment, a pull-string mechanism may be employed to control the size of the proximal opening 320. The pull-string mechanism comprises a string that is woven around the proximal opening 320 and coupled to the capturing basket 300. Pulling on the string reduces the size of the proximal opening while pushing on the string increases the size of the proximal opening 320. An additional locking mechanism may be employed to keep forces on the string from inadvertently opening or closing the proximal opening 320.

As the small pore size of the distal-portion allows that capturing basket 300 to trap pieces of the embolus 105, the pull-string mechanism may be employed to intentionally break up the embolus 105 to create the emboli 105 pieces. The proximal opening 320 may be reduced in size to shear pieces off of a large embolus 105 to make the embolus 105 smaller. The broken piece would be trapped by the distal-portion 305 while the embolus 105, minus the piece, would be smaller and more manageable. Breaking up the embolus 105 may be accomplished in various ways. In one embodiment, the proximal opening 320 is configured to be repeatedly increased in size and reduced in size on an embolus 105 until the embolus 105 shears. The catheter may also be employed to break up the embolus 105 after the proximal opening 320 is closed around the embolus 105.

The capturing basket 300 may be constructed in various ways. In one embodiment the capturing basket is made of braided wire. The wire may be any material suitable to withstand the forces of trapping an embolus 105. In various embodiments, the capturing basket 300 is made of fully radiopaque wire such as platinum. Also, in various embodiments, the capturing basket is made of partially radiopaque wire such as DF Nitinol wire. Also, in various embodiments, the capturing basket is made of non-radiopaque wire such as Nitinol, titanium, Co—Cr alloy, or a polymer. Also, in various embodiments, a combination of different types of wire may be braided to create the capturing basket 300. To create the gradient in pore size, the distal-portion 305 may be made using a micro-braid while the proximal-portion may be made using a large-pore braid. In an exemplary embodiment, the capturing basket 300 may be constructed from tubing that undergoes laser cutting and shape setting. Also, in an exemplary embodiment, the capturing basket may be made by layered deposition using 3D printing. Vapor deposition may also be used to create the capturing basket 300. In various embodiments, the proximal-portion 315 may be made using laser cut and shape set tubing while the distal-portion 305 is micro-braided. The proximal-portion 315 made of laser cut tubing may be coupled to the distal-portion 305 made of micro-braided wire using an interwoven braiding process and/or using a laser welding process.

The inner surface of the capturing basket 300 may be textured using a laser or other means. Texturing imparts roughness to the surface of the capturing basket, which enhances the embolus 105 retention of the capturing basket.

Radiopaque markers may also be employed in the distal-portion 305, mid-portion 310, and proximal-portion 315 to enhance the radiopacity and visualization of the capturing basket 300. The radiopaque markers may be made of radiopaque materials such as platinum or tantalum. The radiopaque markers may be placed strategically around the capturing basket 300 to create visual cues as to the changing shape of the capturing basket 300 as an embolus 105 enters the capturing basket 300. The radiopaque markers may be textured, thus enhancing the embolus 105 retention and visualization of the capturing basket 300.

Figure 3B:
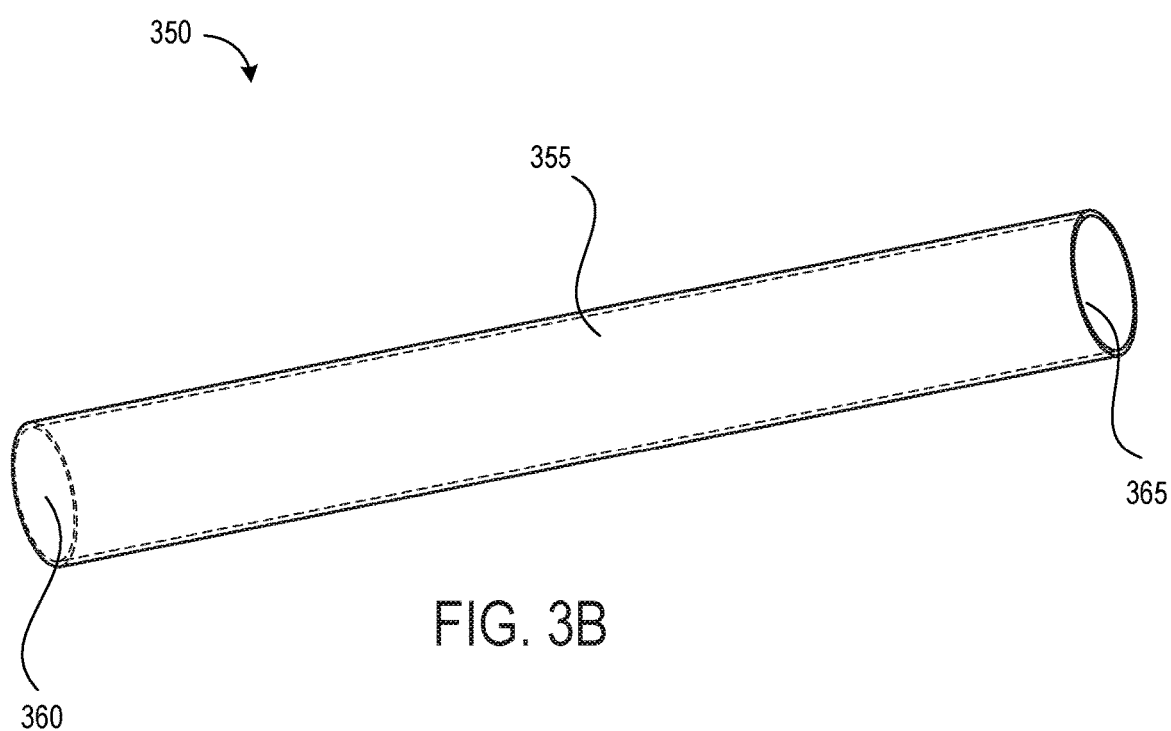
FIG. 3B illustrates an example of a catheter the delivers and retrieves the capturing basket.

Referring to FIG. 3B, FIG. 3B is an illustration of an example of a catheter 350 that may be used to deliver and retrieve the capturing basket 300. The catheter 350 may have a cylinder shaped mid-portion 355, a distal-opening 360, and a proximal opening 365. In various embodiments, the catheter 350 may have a different shape than the shape shown in FIG. 3B.

As shown in FIG. 2, the catheter 350 is configured to contain the capturing basket 300, before the capturing basket 300 is deployed to trap the embolus 105. The catheter may be maneuvered via a guidewire to the site of the embolus 105 from the upstream side of the embolus 105. Once there, the catheter 350 may be pushed across the embolus 105 so that the capturing basket 300 can be deployed on the downstream side of the embolus 105.

Because the capturing basket 300 is expandable, the capturing basket may expand into the shape shown in FIG. 3A after the capturing basket 300 is deployed on the downstream side of the embolus 105. Once the capturing basket 300 traps the embolus 105, the capturing basket 300 may be retrieved back into the catheter 350 so that the catheter 350 and capturing basket 300 may be taken out of the body. The act of retrieving the capturing basket 300 may have the effect of breaking the embolus 105 so that pieces of the embolus 105 fall off and are trapped in the distal-portion 305. In one embodiment, the embolus 105 is intentionally broken up by the repeated retrieval and extrusion of the capturing basket 300 from the catheter 350. Once the embolus 105 is sufficiently broken up, the embolus 105 may be retrieved by a second catheter with a smaller profile.

Figure 4:
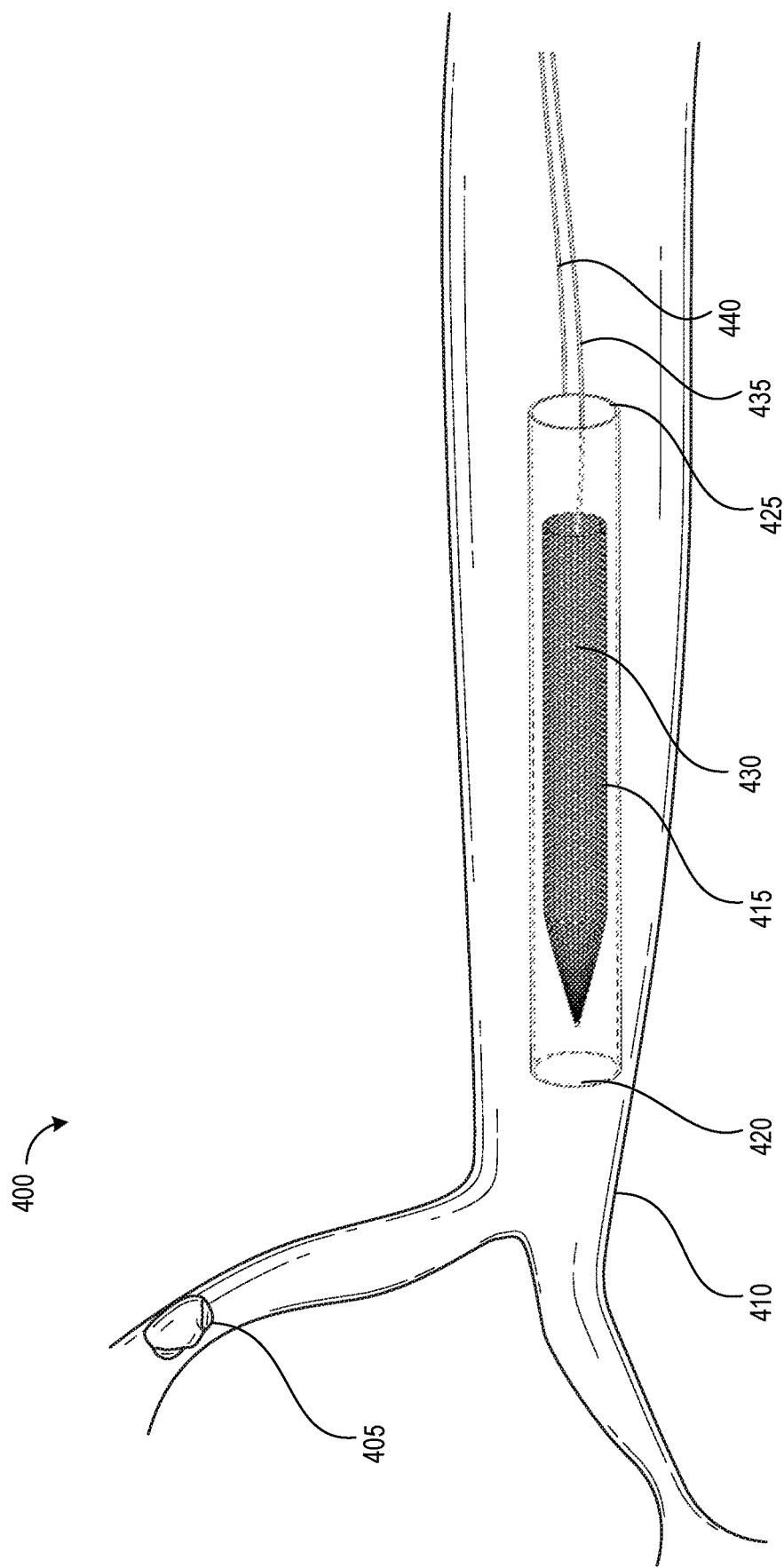
FIG. 4 illustrates an example of the apparatus that has been inserted into a vasculature and directed toward an embolus.

Referring to FIG. 4, FIG. 4 is an illustration 400 of the apparatus that has been inserted into a blood vessel 410 and directed toward an embolus 405. The embolus 405 may have been formed in deep veins such as in the legs. The embolus 405 may travel from the legs through the inferior vena cava, through the heart, and into the pulmonary artery to become lodged in the blood vessel 410. The capturing basket 430 may be conformed to fit inside the catheter 415 as the catheter 415 is delivered to the embolus 405.

A guidewire 440, which is coupled to the proximal opening 425 of the catheter is used to guide the catheter 415 to the site of the embolus 405. Once the catheter 415 is at the site of the embolus 405, the capturing basket 430 may be pushed out of the distal opening 420 of the catheter 415 by a pushwire 435. The pushwire 435 is coupled to the capturing basket 430 through the proximal opening 425 in the catheter 415. The pushwire may also control the pull-string mechanism that reduces and increases the size of the proximal opening 320 of the capturing basket 430.

After the embolus 405 is trapped by the capturing basket 430, the pushwire 435 may be used to pull the capturing basket 430 back into the catheter 430. A locking mechanism may be employed to keep the pushwire from inadvertently increasing the size of the proximal opening 320 of the capturing basket 430 after the embolus is safely trapped within the capturing basket 430. The guidewire 440 may be used to pull the catheter 415 out of the body once the capturing basket 430 has been retrieved by the catheter 415.

Figure 5:
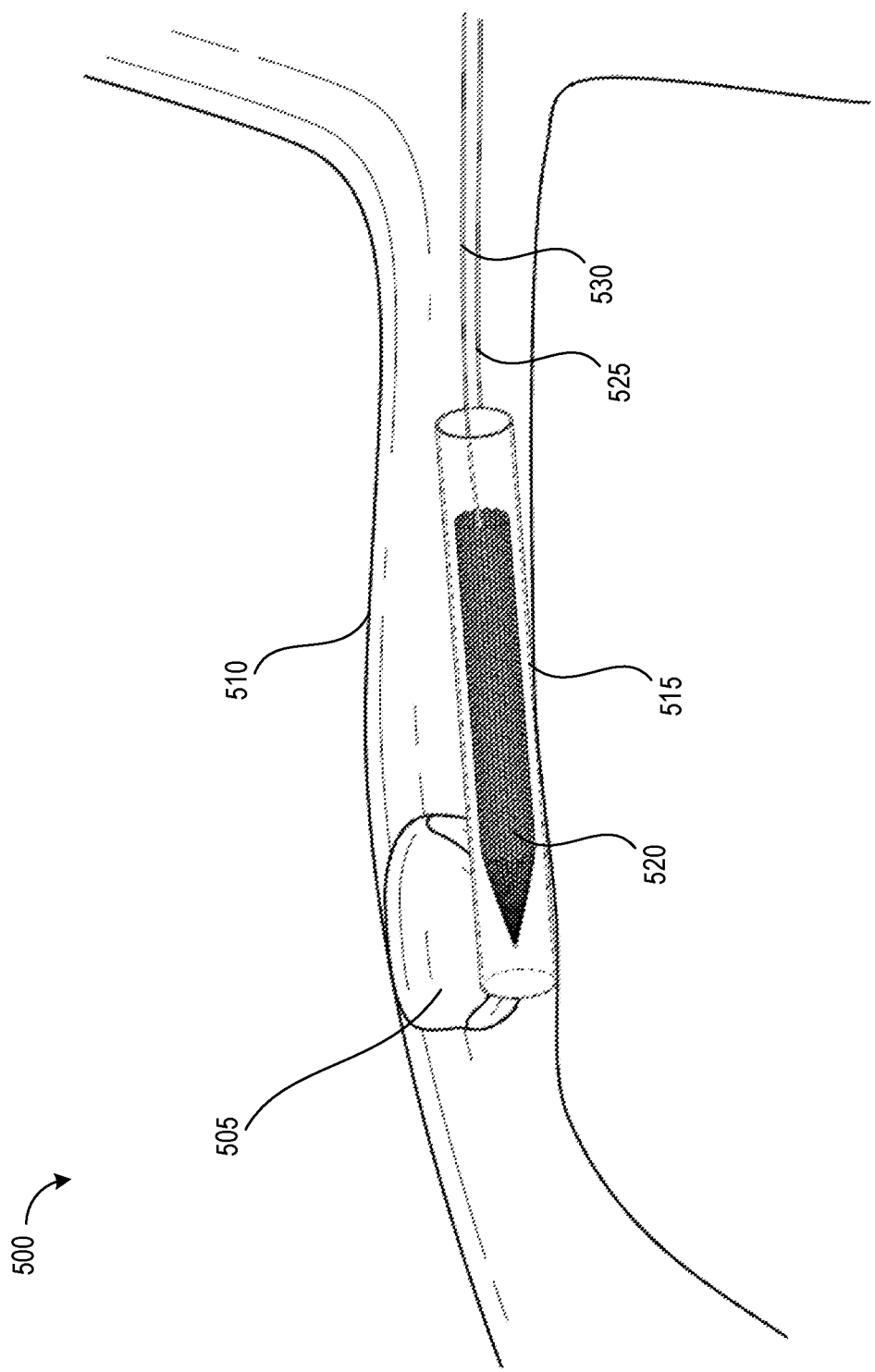
FIG. 5 illustrates an example of the apparatus as the apparatus is pushed across an embolus.

Referring to FIG. 5, FIG. 5 is an illustration 500 of the apparatus as the apparatus is pushed across an embolus 505. The embolus 505 may become lodged or stuck in a blood vessel 510 as the blood vessel 510 gets smaller and smaller. At a certain point, the blood vessel 510 is too small for the embolus 505 and the embolus 505 becomes lodged inside the blood vessel.510.

Typically, the apparatus will be guided to the embolus 505 from the upstream side of the embolus 505. Because the embolus 505 will get clogged in a blood vessel 510 that gets smaller downstream, the upstream side of the embolus 505 is bigger and provides the most accessibility. However, it may be necessary to deliver the capturing basket 520 downstream of the embolus 505 to gain the proper leverage to trap the embolus 505 with the capturing basket 520.

To get the capturing basket 520 downstream of the embolus 505, the apparatus, which includes a catheter 515 and a capturing basket 520 inside the catheter 515, may be pushed across the embolus 505 by the guidewire 530. Force may be used to make space as the apparatus is pushed across the embolus 505 because the embolus 505 is partially or fully blocking the blood vessel 510. Once the distal end of the catheter 515 is exposed to the downstream side of the embolus 505, as shown in FIG. 5, the capturing basket 520 may be pushed out of the distal opening of the catheter 515 by the pushwire 525.

Figure 6:
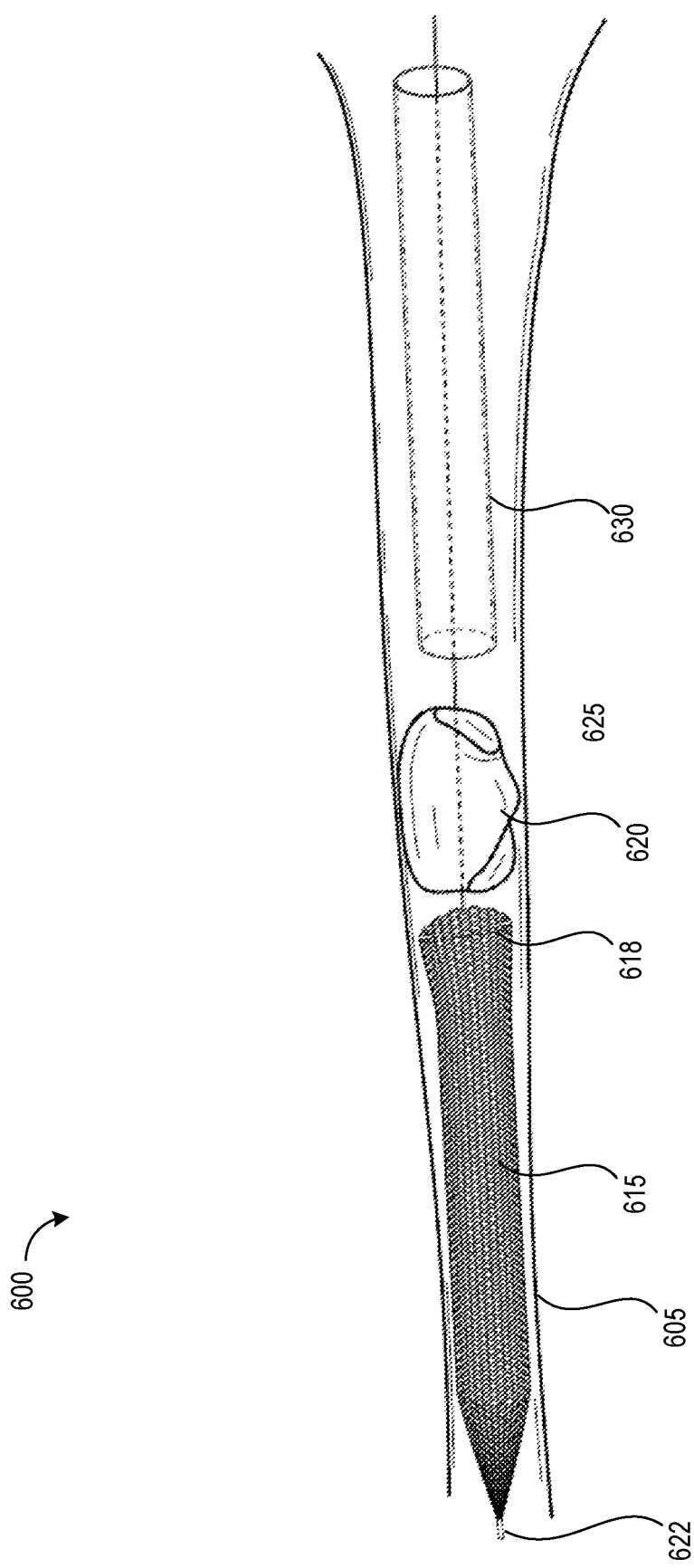
FIG. 6 illustrates an example of the apparatus as the capturing basket has been deployed downstream from an embolus.

Referring to FIG. 6, FIG. 6 is an illustration of the apparatus as the capturing basket 615 has been deployed downstream from an embolus 620 that is lodged in a blood vessel 605. The capturing basket 615 is deployed downstream of the embolus 620 by the catheter 630. As shown in FIG. 5, the catheter 630 may be guided across the embolus 620 by a guidewire such that the distal opening of the catheter is exposed to the downstream side of the embolus 620. The pushwire 625 is then used to push the capturing basket 615 out of the distal opening of the catheter 630.

Once the capturing basket 615 is deployed downstream of the embolus 620, the catheter 630 may be pulled back to the upstream side of the embolus 620. As the capturing basket 615 is expandable, the capturing basket 615 may expand after the capturing basket 615 is pushed out of the catheter 630. In one embodiment, the distal tip 622 of the capturing basket 615 may be made of a soft material. The soft material of the distal tip 622 may be configured to deform when the distal tip 622 contacts the lumen of the blood vessel 605, thus preventing damage to the blood vessel 605. In one embodiment, the capturing basket 615 is sized to have a cross-section that equals or approximates the cross-section of the embolus 620 after the capturing basket is fully expanded. In an exemplary embodiment, as shown in FIG. 6, the cross-section of the capturing basket 615 is slightly smaller than the embolus 620.

Because the capturing basket 615 is configured to be flexible and conform to the shape of the embolus 620, the cross-section of the capturing basket 620 may increase in size in order to trap the embolus 620. The pushwire 625 may be used to adjust the size of the proximal opening 618 in the capturing basket to allow for the embolus 620 to be trapped with the capturing basket 620.

Figure 7:
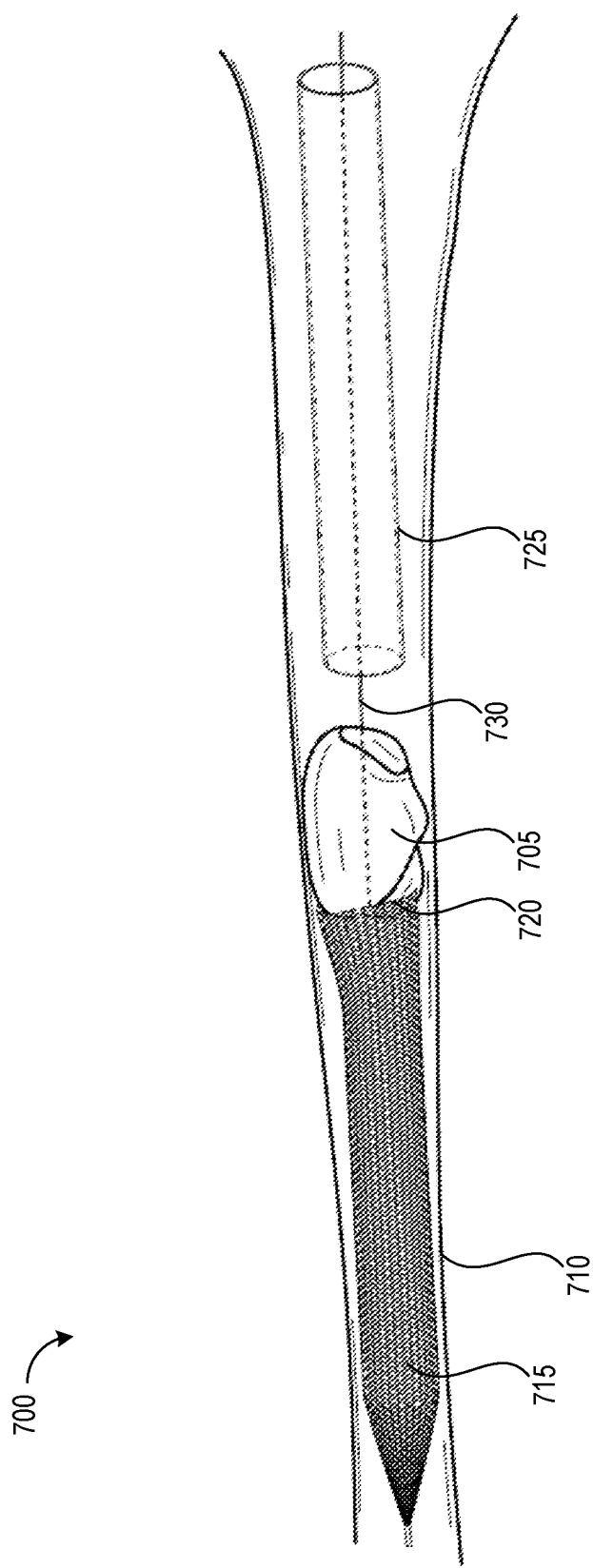
FIG. 7 illustrates an example of the apparatus as the capturing basket is pulled against the embolus.

Referring to FIG. 7, FIG. 7 is an illustration 700 of the apparatus as the capturing basket 715 is pulled against an embolus 705 that is lodged within a blood vessel 710. The size of the proximal opening 720 of the capturing basket 715 may be controlled by the pushwire 730. In the case that a cross-section of the embolus 705 is larger than the proximal opening 720, as shown in FIG. 7, the proximal opening 720 may be increased in size so the capturing basket 715 can receive the embolus 705.

The pushwire 730 may be used to manipulate the size of the proximal opening 720. In addition to the pushwire 730, the environment within the blood vessel 710 may be leveraged to manipulate the size of the proximal opening 720. To leverage the environment within the blood vessel, the pushwire 730 may be used to pull the proximal opening 720 of the capturing basket 715 against the embolus 705. Contact of the embolus 705 with the proximal opening 720 creates force that increases the size of the proximal opening 720. The contact of the proximal opening 720 with the embolus 705 may also act as an anchor to keep the capturing basket 715 in place.

The catheter 725, which was pulled across the embolus 705 to deploy the capturing basket 715 downstream of the embolus 705, may be pulled back upstream of the embolus 705, as shown in FIG. 7. Positioning the catheter 725 upstream of the embolus 705 allows the pushwire 730 which is coupled to the catheter 725 to pull the capturing basket 715 across the embolus 705. The capturing basket 715 may traverse the embolus 705 as the pushwire 725 pulls the capturing basket 715 from the upstream side of the embolus 705.

Figure 8:
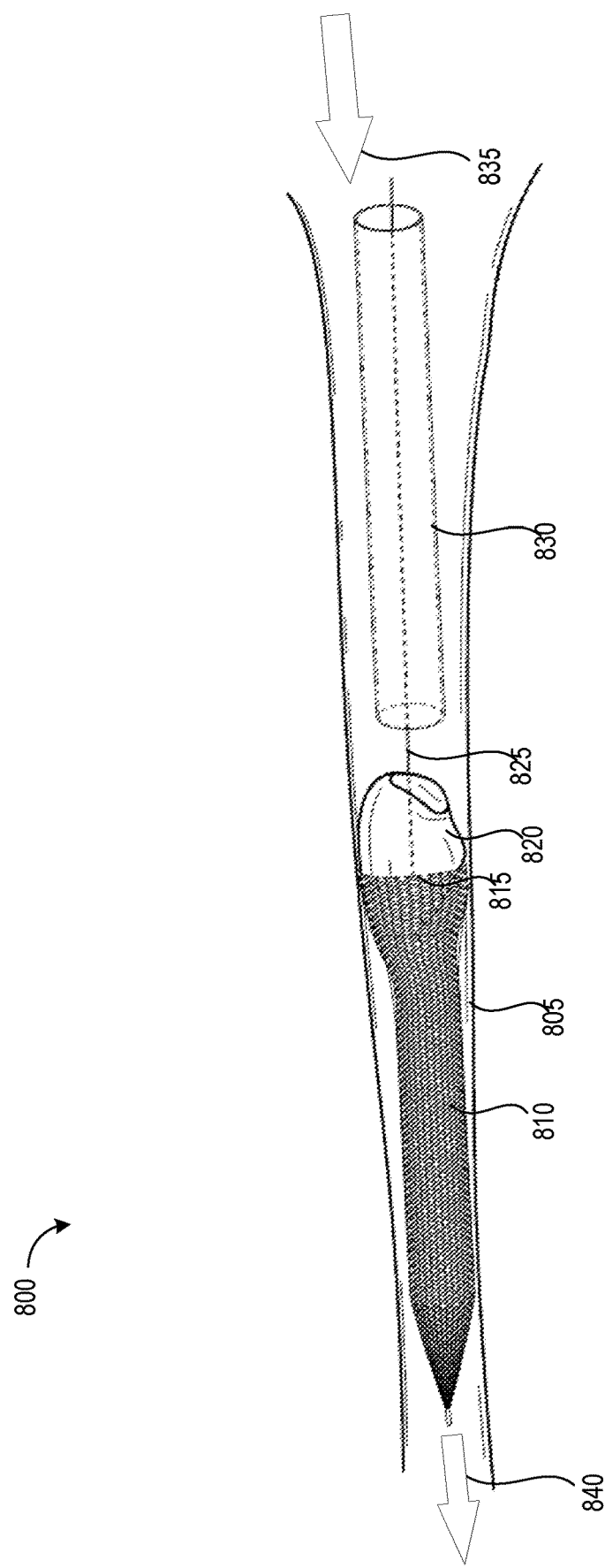
FIG. 8 illustrates an example of the apparatus as the capturing basket partially surrounds the embolus.

Referring to FIG. 8, FIG. 8 is an illustration 800 of the apparatus as the capturing basket 810 partially surrounds the embolus 820. The direction of the flow of blood through the blood vessel 805 is indicated by the arrows on the upstream 835 side of the embolus 820 and the downstream 840 side of the embolus 820. As shown in FIG. 8, the pushwire 825 may be pulled from upstream 835 of the embolus 820 to create the leverage needed for the capturing basket 810, which is downstream 840, to traverse and surround the embolus 820. The pushwire 825 is coupled to the catheter 830, which is also upstream 835 of the embolus 820.

The proximal opening 815 may be increased in size, as shown in FIG. 8, to surround an embolus 820 that has a larger cross-section than the diameter of the capturing basket 815. Similarly, the portion of the capturing basket 810 that surrounds the embolus 820 may increase in diameter as the capturing basket 810 conforms to the shape of the embolus 820. The length of the capturing basket 810 may become shorter as the braided wire of the capturing basket 810 conforms to the large size of the embolus 830.

If the capturing basket 810 is made of radiopaque material, imaging of the capturing basket 810 may indicate that the embolus 820 is inside the capturing basket 810. In the illustration 800, the embolus 820 is only partially inside the capturing basket 815. Under imaging, which typically does not show the embolus 820, the increased size of the capturing basket 810 in the proximal-portion 315 and increased size of the proximal opening 815 indicates that the embolus 820 is only partially surrounded by the capturing basket 815.

When the embolus 820 is partially surrounded, the proximal opening 815 may be used to shear the embolus 820. Reducing the size of the proximal opening 815 while the embolus 820 is partially surrounded may shear the embolus 820. In one embodiment, the proximal opening 815 of the capturing basket 810 is configured to be repeatedly increased in size and reduced in size. The repeated action of increasing and reducing the size of the proximal opening 815 on the partially surrounded embolus 820 may gradually shear an embolus 820 that is otherwise resistant to shearing. The pieces of the embolus 820 that shear off may be caught in the mid-portion 310 and/or distal portion 305 of the capturing basket 810. Once the embolus is sheared 820, the embolus 820 may be smaller and more manageable to retrieve from the body. The proximal opening 820 may also be used to latch onto the partially surrounded embolus 820 and pull the embolus upstream 835.

Figure 9:
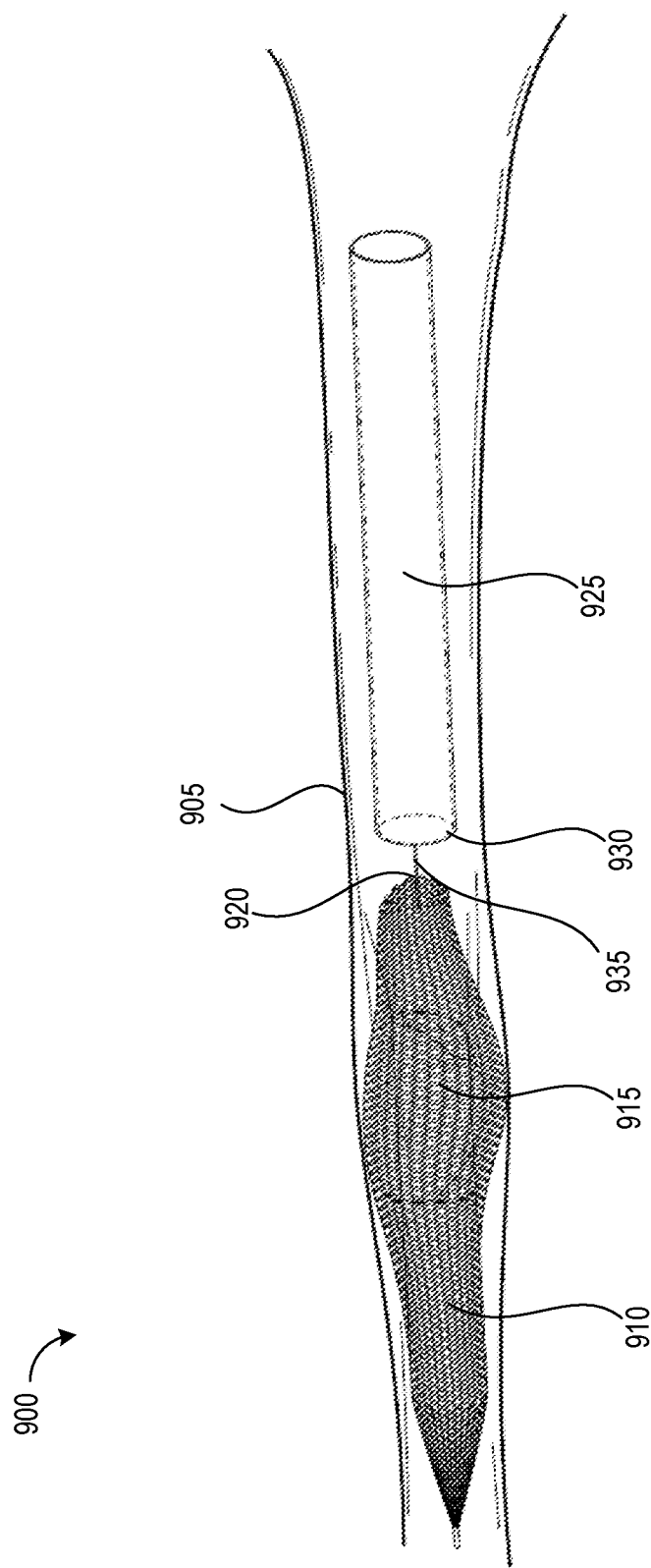
FIG. 9 illustrates an example of the apparatus after the capturing basket has completely surrounded the embolus.

Referring to FIG. 9, FIG. 9 is an illustration 900 of the apparatus after the capturing basket 910 has completely surrounded the embolus 915. In various embodiments, the capturing basket 910 is made of fully radiopaque materials or partially radiopaque materials. Imaging of the partially or fully radiopaque capturing basket 910 may indicate that the embolus 915 is completely surrounded by the capturing basket 910.

An indicator that the capturing basket 915 has surrounded the embolus 915 may be the shape of the capturing basket 910 as the capturing basket conforms to the shape of the embolus 915. Another indicator that the embolus 915 has been surrounded by the capturing basket 910 is that the proximal opening 920 and part of the diameter of the proximal-portion of the capturing basket 910 have reduced in size. Yet another indicator that the embolus 915 is trapped within the capturing basket 910 is that the length of the capturing basket 910 becomes shorter as a result of the capturing basket 910 conforming to the shape of the embolus 915. Yet another indicator that the capturing basket 915 has surrounded the embolus 915 may be that the capturing basket 910 can be freely pulled upstream from the original location of the embolus 915 in the blood vessel 905. Because radiopaque markers may not be placed in all parts of the capturing basket 910, some indicators may not be applicable in all circumstances.

Once the proximal opening has closed and trapped the embolus 915, a locking mechanism may be employed to keep the proximal opening 920 from being inadvertently opened. The pushwire 935, which controls the size of the proximal opening 920, may therefore be safely used to pull the capturing basket upstream. The capturing basket 910 may be drawn toward the catheter 925 by the pushwire 935. The pushwire 935 is coupled to the catheter 925 at the distal opening 930 of the catheter 925. Therefore, the pushwire 935 may be employed to pull the capturing basket to the distal opening to the catheter 925 for eventual retrieval of the capturing basket 910 and embolus 915 from the body.

Figure 10:
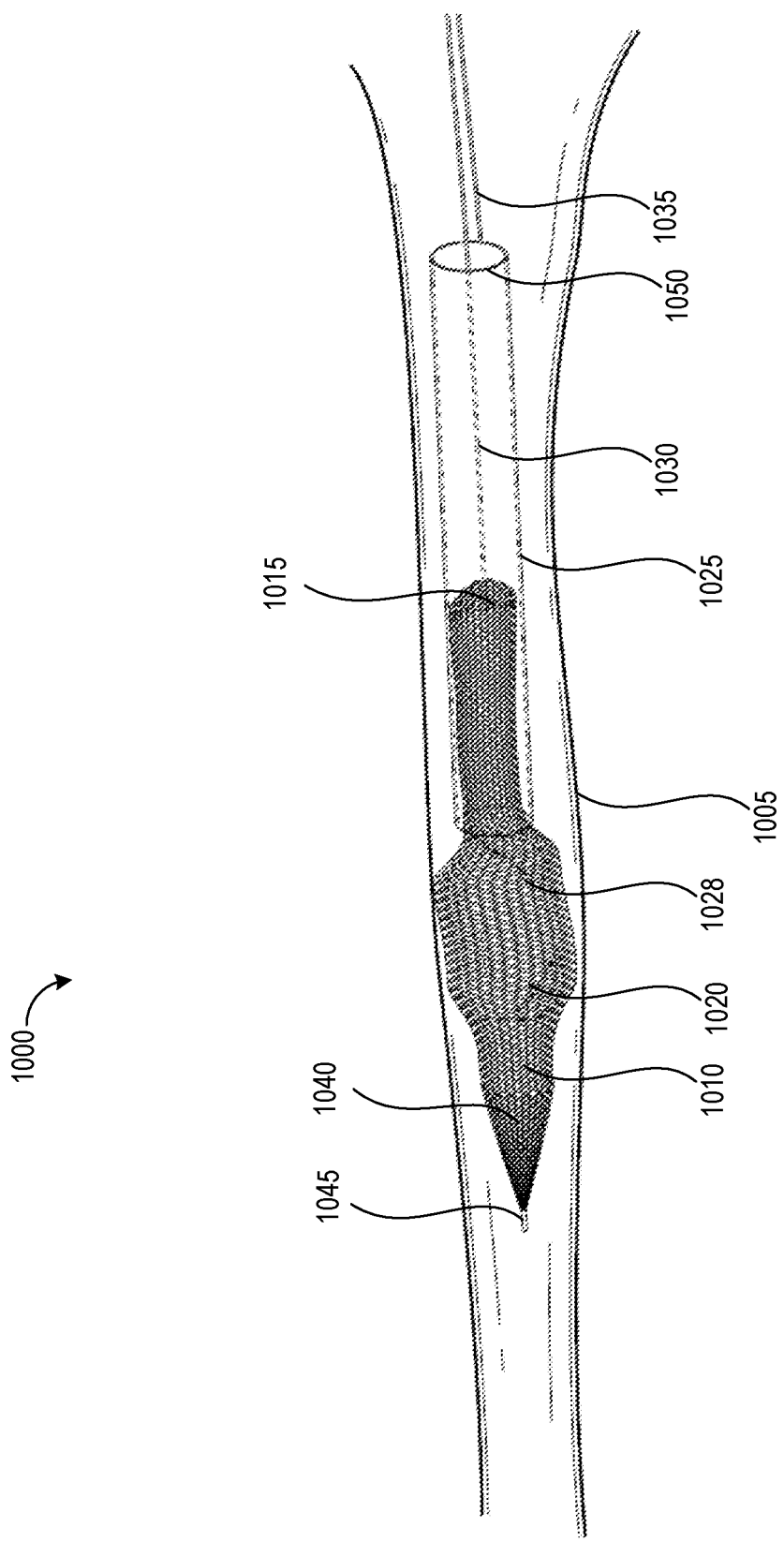
FIG. 10 illustrates an example of the apparatus as the capturing basket is being forced into the catheter.

Referring to FIG. 10, FIG. 10 illustrates an example of the apparatus as the capturing basket 1010 is being forced into the catheter 1025. Once the capturing basket 1010 has fully surrounded the embolus 1020, the capturing basket 1010 may be drawn into the catheter 1025 by the pushwire 1030. Because the pushwire 1030 controls the size of the proximal opening 1015 of the capturing basket 1010, a locking mechanism may be employed to prevent the pushwire 1030 from manipulating the size of the proximal opening 1015 as the pushwire 1030 is used to pull the capturing basket into the catheter 1030. Aspiration at the proximal opening 1050 of the catheter 1025 may be used to aid in pulling the embolus 1020 into the catheter 1025.

As shown in FIG. 10, the catheter 1025 may have a smaller diameter than the cross-section of the embolus 1020. The embolus 1020 may be squeezed into the distal opening 1028 of the catheter 1025 for retrieval. In some cases, the embolus 1020 may break apart as the embolus 1020 is pulled through the distal opening 1028 of the catheter 1025. Pieces of the embolus 1020 that break from the embolus 1020 may be trapped by the distal portion 1040 of the capturing basket.

To aid in reducing the profile of the embolus 1020, the capturing basket 1010 with trapped embolus 1020 may be repeatedly pulled into the distal opening 1028 of the catheter 1025 and then extruded back through the distal opening 1028. While using the locking mechanism to prevent manipulation of the proximal opening 1015 of the capturing basket 1010, the pushwire 1030 may be used to repeatedly pull the capturing basket 1010 into the catheter 1025 and then extrude the capturing basket 1020 from the catheter 1025. The repeated extrusion of the trapped embolus 1020 may gradually reduce the profile of the embolus 1020. The embolus 1020 with a reduced profile may be fully pulled into the catheter 1025 or retrieved by a lower profile catheter.

There may be an increased risk of puncturing the inner lumen of the blood vessel 1005 as force is being applied to the apparatus to retrieve the capturing basket 1010 into the catheter 1025. Therefore, the guidewire may be used to pull the apparatus to a larger blood vessel where there is less chance of puncturing a blood vessel. The soft distal tip 1045 of the capturing basket 1010 may also help prevent inadvertent puncturing of the blood vessel 1005.

Figure 11A:
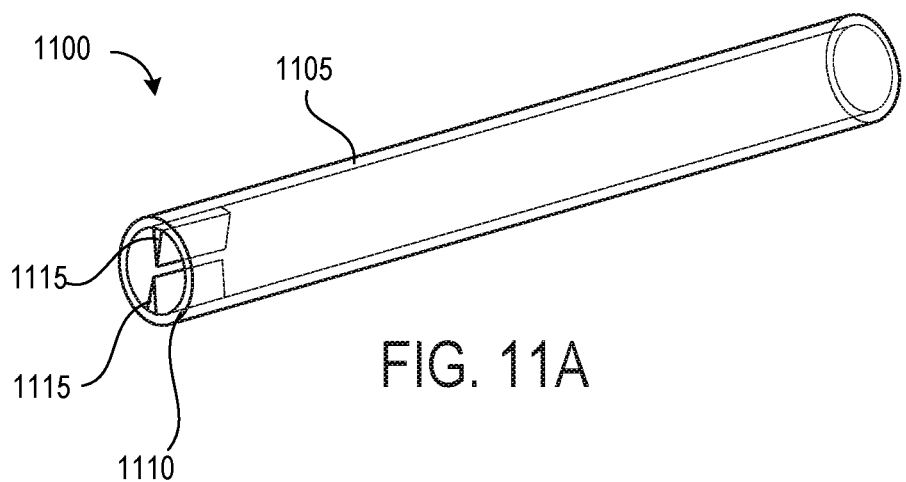
FIG. 11A illustrates an embodiment of the catheter that comprises sharp edges at the distal end.

Referring to FIG. 11A, FIG. 11A is an illustration 1100 of an embodiment of the catheter 1105 that comprises sharp edges 1115 at the distal portion 1110 of the catheter 1105. In one embodiment of the apparatus shown in FIG. 11A, sharp edges 1115 are contained in the inner lumen of the catheter 1105. The sharp edges 1115 are configured to cut the embolus 105 as the embolus 105 is captive within the capturing basket 300. The sharp edges 1115 may be used when the capturing basket 300 is partially or fully within the catheter 1105. An example of the capturing basket being partially within the catheter 1105 is shown in FIG. 10.

The sharp edges 1115 may be retracted until the trapped embolus 105 is pulled into the catheter 1105. The sharp edges 1115 may be activated by a pushwire that is separate from the pushwire that is coupled to the capturing basket 300. In one embodiment, the catheter 1105 is configured to have the sharp edges 1115 activated after the trapped embolus 105 is pulled into the catheter 1105. Activation of the sharp edges 1115 may be performed in tandem with repeated extrusion of the embolus 105 from the catheter 1115. The repeated extrusion of the embolus 105 used in combination with activation of the sharp edges 1115 may reduce the profile of an embolus 105 to allow for easy retrieval from the body.

Activation of the sharp edges 1115 may break or shear pieces of the embolus 105. Pieces of the embolus 105 that break from the embolus 105 may be trapped by the distal-portion 305 and mid-portion 310 of the capturing basket. As pieces of the embolus 105 break away, the embolus 105 gradually becomes smaller and more manageable. In some cases, a large embolus 105 may be intentionally sheared until the embolus 105 is small enough to be safely retrieved from the body. The capturing basket 300 may be configured to resist being sheared by the sharp edges 1115.

Figure 11B:
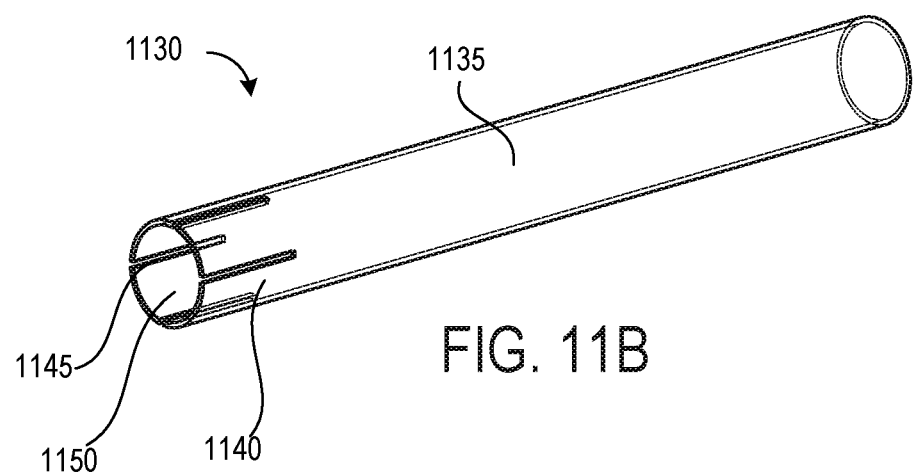
FIG. 11B illustrates an embodiment of the catheter that comprises slits at the distal end that facilitate a widening of the distal end.
Figure 12:
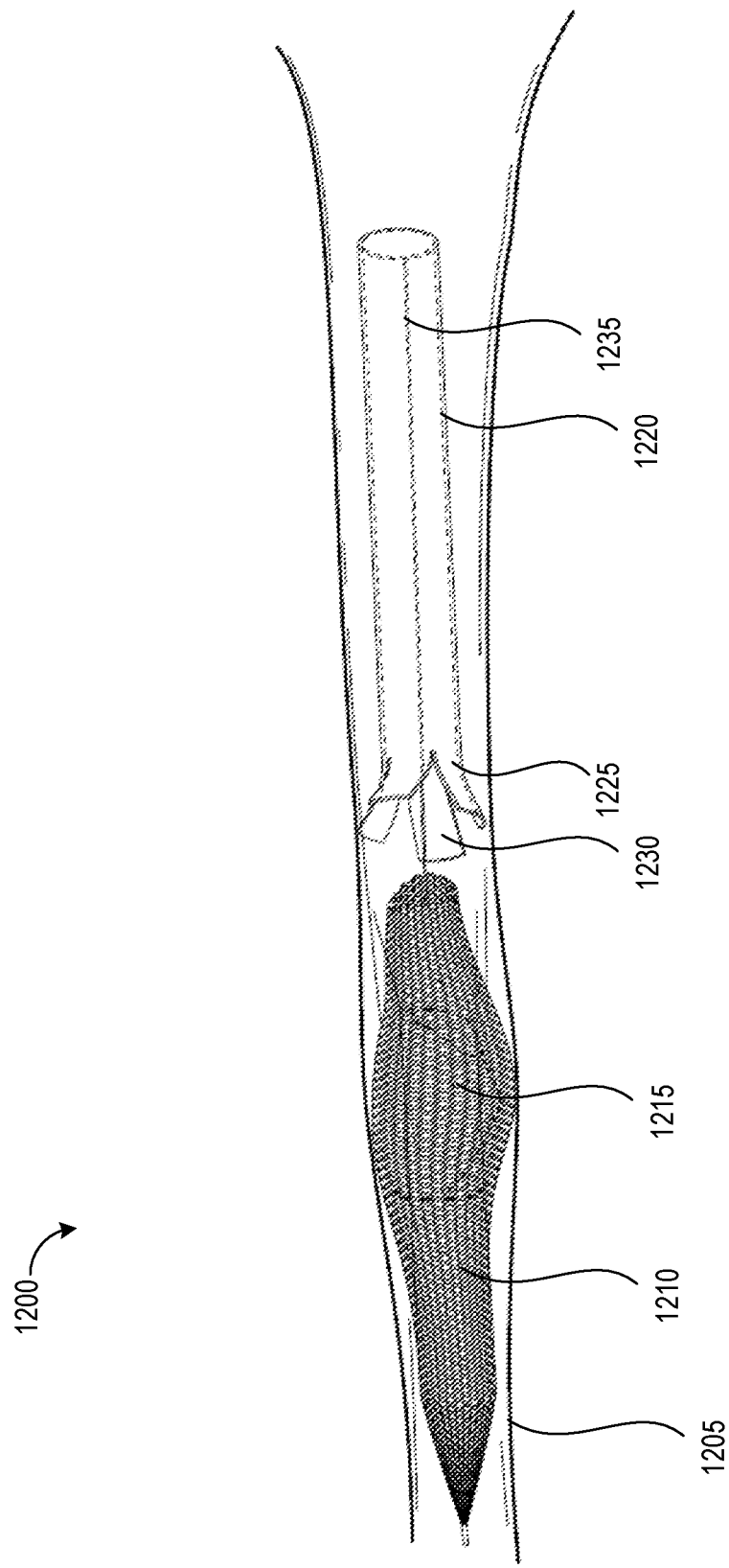
FIG. 12 illustrates an example of the apparatus as the distal end of the catheter is widened to retrieve a capturing basket that has surrounded an embolus.

Referring to FIG. 11B, FIG. 11B is an illustration 1130 of a catheter 1135 with slits 1145 at the distal end 1140. The purpose of the slits 1145 is to allow the distal end 1140 to increase in size and/or decrease in size. The illustration 1130 shows five slits 1145 in the distal end 1140 of the catheter 1135. The 5 slits 1145 create 5 rectangular surfaces 1150 at the distal end 1140. The slits 1145 allow the rectangular surfaces 1150 to be tilted toward or away from a central axis of the catheter 1135, which runs down the center of the cylindrical shape of the catheter 1135. The distal end 1140 increases in size when the rectangular surfaces 1150 tilt away from the central axis. Likewise, the distal end 1140 decreases in size when the rectangular surfaces 1150 tilt toward the central axis of the catheter 1135. An example of the rectangular surfaces being tilted away from the central axis of the catheter 1135 is shown in FIG. 12.

The action to increase or decrease the size of the distal end 1140 may be effectuated by mechanical actuation or mechanical movement of actuate wires. The actuate wires may be operated by a proximal handle coupled to the catheter 1135. In an exemplary embodiment, a balloon catheter is used to apply pressure that results in the distal end 1140 increasing in size.

In one embodiment, the distal end 1140 is increased in size to aid in retrieving the capturing basket 300 that has trapped an embolus 105. The increased size of the distal end 1140 allows the catheter 1135 to retrieve a capturing basket 300 with a larger cross section than the diameter of the catheter 1135. Additionally, the distal end 1140 acts as a funnel when the rectangular surfaces 1150 are tilted away from the central axis of the catheter. In an exemplary embodiment, the distal end 1140 is decreased in size to soften and break emboli 105 that are trapped within the capturing basket 300. Also, in an exemplary embodiment, the distal end 1140 may be configured to repeatedly decrease and increase in size to soften an embolus 105.

Figure 11C:
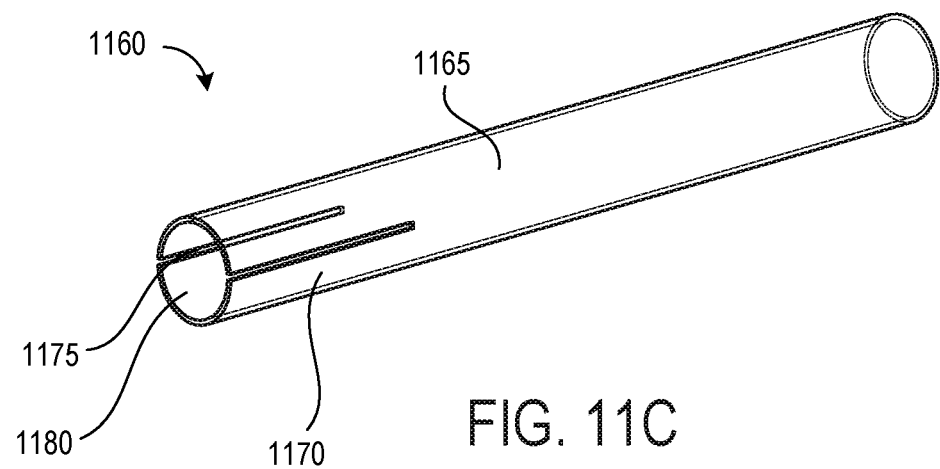
FIG. 11C illustrates an embodiment of the catheter that comprises slits at the distal end that facilitate a widening of the distal end.

Referring to FIG. 11C, FIG. 11C is an illustration 1160 of an embodiment of a catheter 1165 with two slits 1175 at the distal end 1170 of the catheter 1165. The slits 1175 create two curved rectangular surfaces 1180. Like the catheter 1135 shown in FIG. 11B, the slits 1175 allow the distal end 1170 to be increased in size or decreased in size by tilting the curved rectangular surface away from and toward the central axis of the catheter 1165.

As the distal end 1170 is increased in size, a capturing basket 300 with trapped embolus 105 may be directed into the catheter 1165 more easily than if the size of the distal end 1170 remained unchanged. Once a capturing basket 300 is between the two curved rectangular surfaces 1180, the curved rectangular surfaces 1180 may be tilted toward the central axis of the catheter 1165 to squeeze and break up the trapped embolus 105. The distal end 1170 may be configured to repeatedly increase and decrease in size while an embolus 105 is trapped in the capturing basket 300 between the curved rectangular surfaces 1180.

Referring to FIG. 12, FIG. 12 is an illustration 1200 of the apparatus as the distal end 1225 of the catheter 1220 is increased in size to retrieve a capturing basket 1210 that has surrounded an embolus 1215. In one embodiment of the catheter 1220 which is shown in FIG. 12 and FIG. 11B, the catheter 1220 has slits 1145 in the distal end 1225, which allow the rectangular surfaces 1230 created by the slits 1145 to be tilted toward the central axis of the catheter 1220 or away from the central axis of the catheter 1220. The rectangular surfaces 1230 in FIG. 12 are tilted away from the central axis of the catheter 1220, which effectively increases the diameter of the opening at the distal end 1225 of the catheter 1220. In addition to effectively increasing the diameter of the opening at the distal end 1225 of the catheter 1220, the rectangular surfaces 1230 create a funnel-like shape, which directs a volume within the rectangular surfaces 1230 into the opening at the distal end 1225 of the catheter 1220.

The funnel-like shape of the distal end 1225 allows the trapped embolus 1215 to be gradually squeezed into the catheter 1220. As shown in FIG. 10, directing the trapped embolus 1020 in the catheter results in an abrupt change in the size of the cross-section of the embolus 1020 at the distal opening 1028. The large force required to effect the abrupt change in the size of the cross-section of the embolus 1028 may be lowered by the catheter 1220 shown in FIG. 12. The funnel-like shape of the distal end 1225 may result in a gradual change in the size of the cross section of the embolus 1215 as the embolus 1215 is pulled into the catheter 1220, which may lower the force required to pull the embolus 1215 into the catheter 1220.

Once the trapped embolus 1215 is within the volume created by the rectangular surfaces 1230, the rectangular surfaces 1230 may be further tilted to aid in the retrieval of the trapped embolus 1215. In one embodiment, the rectangular surfaces 1230 are configured to be repeatedly tilted toward the central axis of the catheter 1220 and away from the central axis of the catheter 1220. The repeated tilting of the rectangular surfaces 1230 may soften the trapped embolus 1215 to eventually allow the profile of the trapped embolus 1215 to be reduced enough to retrieve the trapped embolus 1215.

Figure 13:
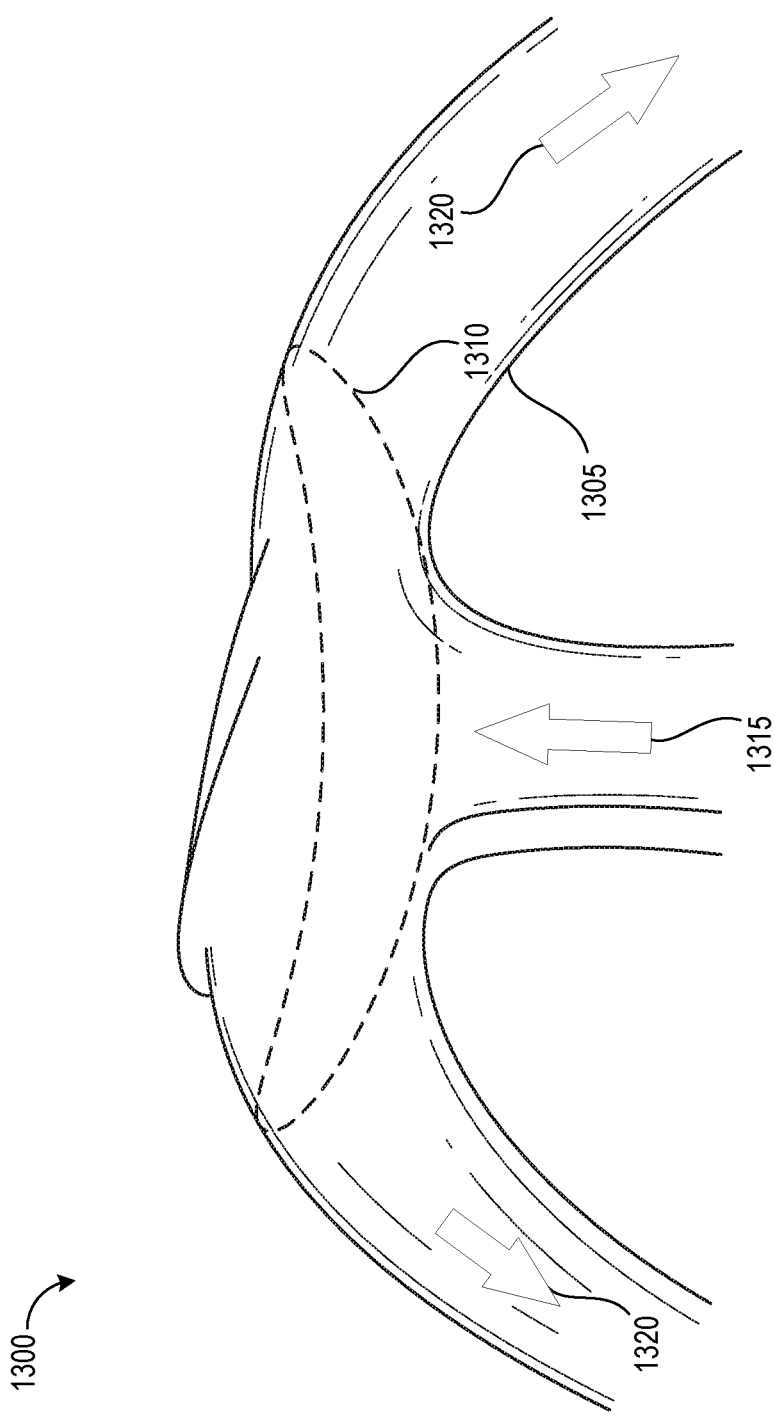
FIG. 13 illustrates an example of a saddle embolus.

Referring to FIG. 13, FIG. 13 is an illustration 1300 of a saddle embolus 1310 that is trapped within a blood vessel 1305. The saddle embolus 1310 becomes lodged at a point where the blood vessel 1305 bifurcates and blocks the entrance to a bifurcated portion of the blood vessel 1305. The saddle embolus 1310 may be lodged at a point that the pulmonary artery 130 bifurcates into the right pulmonary artery 135 and the left pulmonary artery.

Saddle emboli 1310 may become large enough to obstruct the flow of blood to both bifurcated portions of the blood vessel 1305. In some cases, the saddle embolus 1310 may be trapped by a capturing basket 300 similarly to an embolus that is lodged in a non-bifurcating blood vessel. The capturing basket 300 may approach the saddle embolus 1305 from the upstream 1315 blood vessel. The direction of blood flow is represented by the upstream 1315 and downstream 1320 arrows. If the saddle embolus 1305 is at the bifurcation of the pulmonary artery 130, the pulmonary artery 130 is upstream 1315 of the saddle embolus while the right pulmonary artery 135 and left pulmonary artery 140 are downstream 1320 of the saddle embolus 1305.

Figure 14:
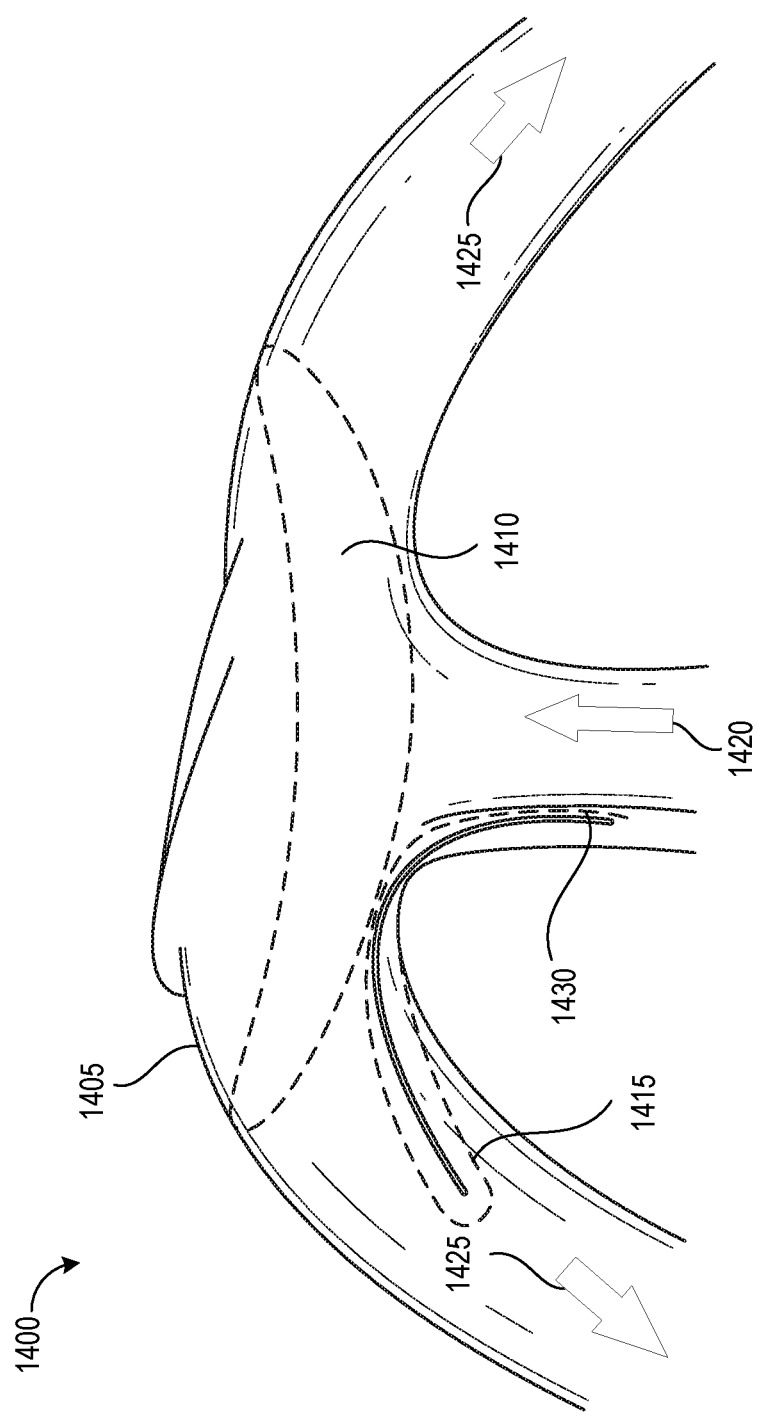
FIG. 14 illustrates an example of the apparatus as the apparatus is pushed across the saddle embolus.

Referring to FIG. 14, FIG. 14 is an illustration 1400 of the apparatus 1415 as the apparatus 1415 is pushed across a saddle embolus 1410. The apparatus 1415, which includes the capturing basket 300 may also include the catheter 350. The apparatus 1415 may be delivered from an upstream 1420 portion of the blood vessel 1405 by a guidewire 1430.

The guidewire 1430 may be used to push the apparatus to a downstream 1425 portion of the blood vessel. Since there are two downstream 1425 portions of the blood vessel 1405, which is bifurcated, the preferred downstream 1425 portion may depend on various factors such as the shape and position of the saddle embolus 1405. If the saddle embolus 1405 is completely blocking the blood vessel 1405, force may be applied to the guidewire 1430 to push through the blood vessel 1405 that is blocked.

Once the apparatus 1415 is in a position on the downstream 1425 portion of the saddle embolus 1410, the capturing basket on the apparatus 1415 may be deployed. In one embodiment, the capturing basket is deployed by pushing the capturing basket with a pushwire out of a catheter. The pushwire may be a separately manipulatable wire that is adjacent to the guidewire 1430. The capturing basket may be deployed on the downstream 1425 portion of the saddle embolus 1410 so that the capturing basket may be pulled back to traverse and trap the saddle embolus 1410.

Figure 15:
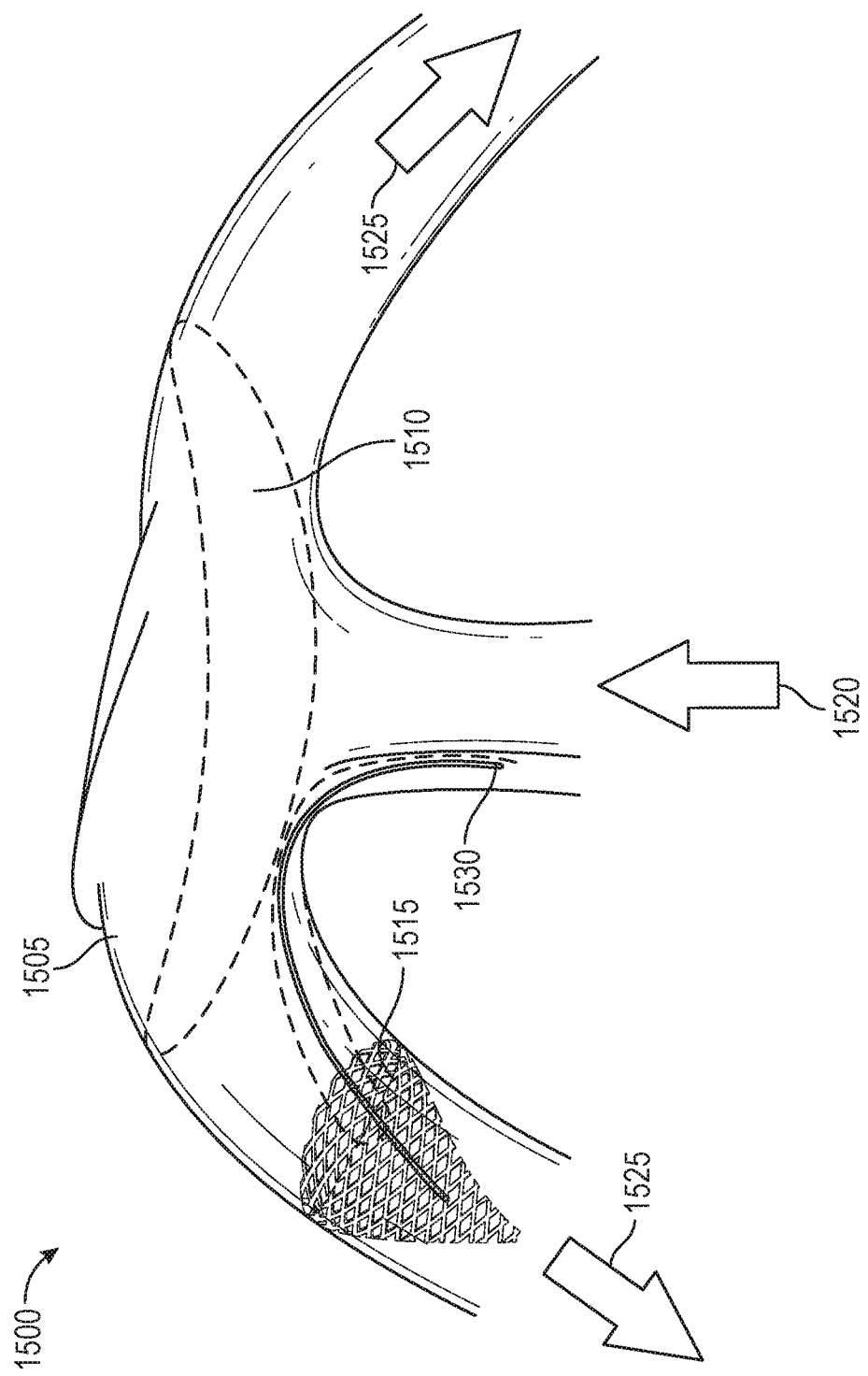
FIG. 15 illustrates an example of the apparatus as the capturing basket has been deployed next to the saddle embolus.

Referring to FIG. 15, FIG. 15 is an illustration 1500 of the apparatus as the capturing basket 1515 has been deployed next to the saddle embolus 1510. Prior to being deployed, the apparatus may be pushed across the saddle embolus 1510 from the upstream side 1520 to a downstream side 1525 of the saddle embolus 1510 by a guidewire 1530. The guidewire 1530 may be used to position the apparatus in a suitable location to deploy the capturing basket 1515.

In one embodiment, the capturing basket 1515 may be made of a material that is expandable into a predetermined shape, such as Nitinol wire. The capturing basket 1515, made of Nitinol wire, may be deformed below a transition temperature. The capturing basket 1515, in its deformed state, may be packaged with a small profile that is ideal for delivery into the body. When the capturing basket 1515, made of Nitinol wire, is brought above the transition temperature, the capturing basket 1515 expands to its original shape. The original shape of the capturing basket 1515 may be various shapes, such as the basket-like shape shown in FIG. 15, that efficiently traps the saddle embolus 1510.

The proximal opening of the capturing basket 1515 may be configured to increase in size to a diameter that matches the cross-section of the saddle embolus 1510. A pushwire may be used to adjust the size of the proximal opening to the most advantageous size. An additional locking mechanism may be implemented to prevent a inadvertent change in size of the proximal opening of the capturing basket 1515. Once the capturing basket 1515 has been deployed and positioned on the downstream side 1525 of the saddle embolus 1510 and the proximal opening has been adjusted to the most advantageous size, the capturing basket 1515 may be pulled toward the saddle embolus 1510. The capturing basket 1515 may be pulled to completely surround or partially surround the saddle embolus 1510. The proximal opening of the capturing basket 1515 may be reduced in size to trap the saddle embolus 1510 once the capturing basket 1515 has surrounded the saddle embolus 1510.

Figure 16:
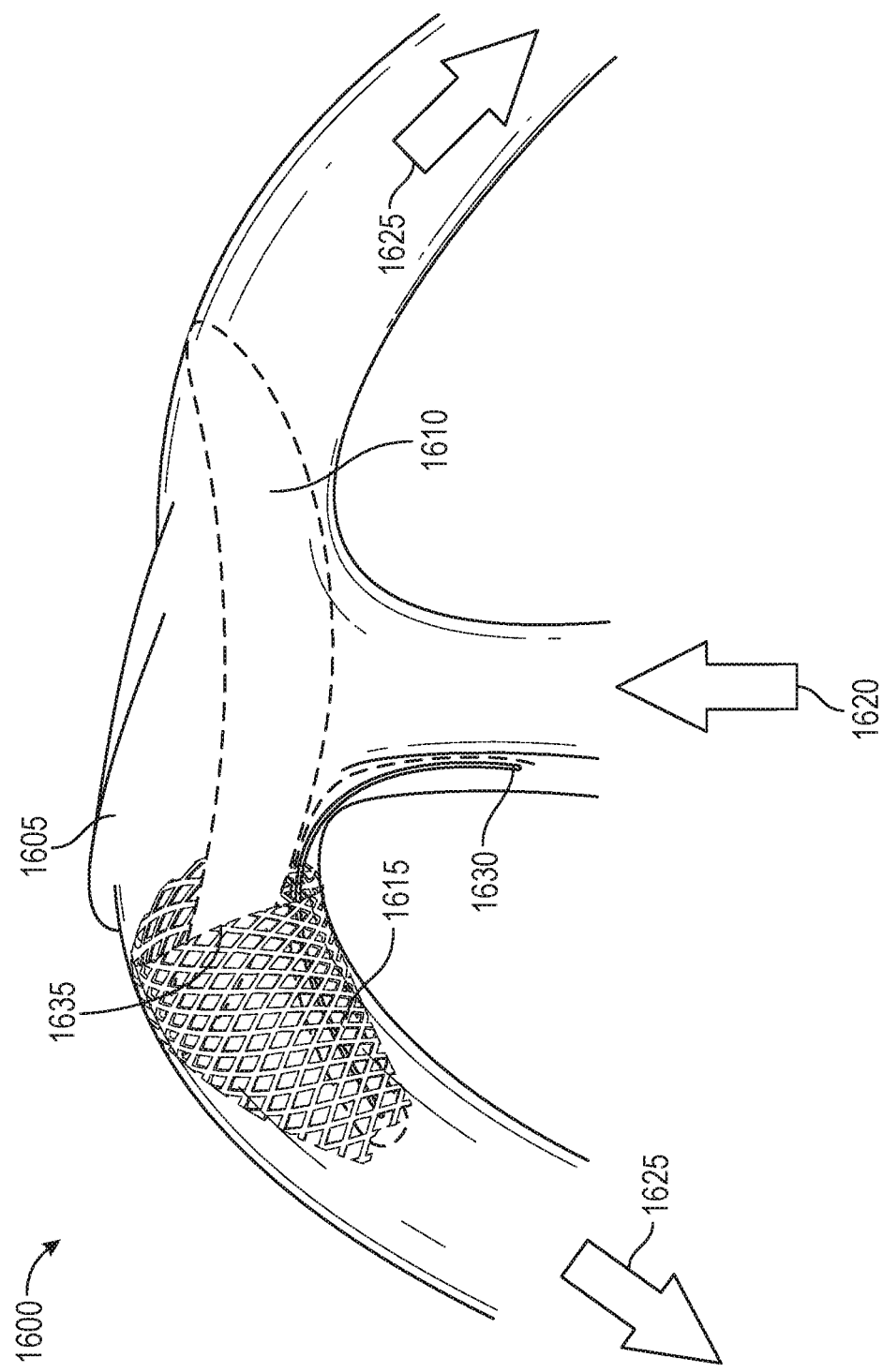
FIG. 16 illustrates an example of the apparatus as the capturing basket has partially surrounded the saddle embolus.

Referring to FIG. 16, FIG. 16 is an illustration 1600 of the saddle embolus 1610 after the capturing basket 1615 has partially surrounded the saddle embolus 1610. After the capturing basket 1615 has been deployed on the downstream side 1625 of the saddle embolus 1610, the capturing basket 1615 may be pulled to surround and traverse the saddle embolus 1615 as shown in FIG. 16. The proximal opening 1635 of the capturing basket 1615 may be reduced in size to trap the saddle embolus 1615. The guidewire 1630, which is manipulated from the upstream side 1620 of the saddle embolus 1610 may be used to pull the saddle embolus 1610 in the upstream direction of the blood vessel 1605 to eventually retrieve the saddle embolus 1615 from the body.

The capturing basket 1615 may be made with wire or metal tubing that is radiopaque or partially radiopaque. The radiopaque or partially radiopaque materials allow the capturing basket 1615 to be seen through imaging such as fluorescent imaging when the capturing basket 1615 is within the body. In addition to making the capturing basket 1615 with radiopaque materials, the capturing basket 1615 may have radiopaque markers that are positioned at locations in the capturing basket 1615 that allow a user to visualize the profile of the capturing basket 1615 under imaging. The capturing basket 1615 may be configured to conform to the shape of the saddle embolus 1610, which in turn displays an image of the shape of the saddle embolus 1610. As the size of the saddle embolus 1610 may be difficult to ascertain through other non-invasive means, radiopaque markers in the capturing basket 1615 may help elucidate the size and shape of the saddle embolus 1610.

Once the saddle embolus 1610 has been trapped by the capturing basket 1610, the saddle embolus 1610 may be moved and retrieved from the body. Alternatively, the saddle embolus 1610 may be reduced by shearing pieces from the saddle embolus 1610. In some cases the, saddle embolus 1610 may be too big to safely retrieve from the body until the saddle embolus has been reduced. The saddle embolus 1610 may be reduced in various ways. In one example the proximal opening 1635 of the capturing basket 1615 is reduced in size to shear the portion of the saddle embolus 1610 that is within the capturing basket 1615. Pieces of the saddle embolus 1610 that are sheared by the proximal opening 1635 may be trapped in the mid-portion or the distal portion of the capturing basket 1615.

Figure 17A:
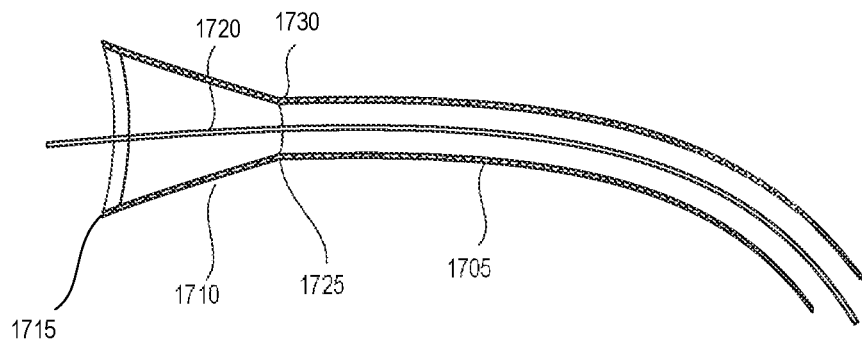
FIG. 17A is an illustration of an embodiment of the embolus retrieving apparatus that includes an inflatable balloon catheter.

Referring to FIG. 17A, FIG. 17A is an illustration 1700 of an embodiment of the embolus retrieving apparatus that includes an inflatable balloon catheter 1715. The inflatable balloon catheter 1715 has a surface with an open distal end 1715 and an open proximal end 1725. To reduce the profile of the inflatable balloon catheter 1705, the inflatable balloon catheter 1705 may be delivered to the location of an embolus while the inflatable balloon catheter 1705 is in a deflated state. The shape of the inflatable balloon catheter 1705, while in the inflated state, helps retrieve the capturing basket by directing the capturing basket into the catheter 1705.

The large distal opening of the inflatable balloon catheter 1710 facilitates the retrieval of the capturing basket once the capturing basket has surrounded an embolus. In one embodiment, shown in FIG. 17A, the proximal end 1725 of the inflatable balloon catheter 1705 is smaller than the distal end 1715 of the inflatable balloon catheter 1715. The capturing basket, after surrounding an embolus, may be larger than the distal opening 1730 of the catheter 1705. The guidewire 1720 is used to pull the capturing basket, that has surrounded an embolus, into the inflatable balloon catheter 1715. The funnel shape of the inflatable balloon catheter 1715 may be leveraged to contract the capturing basket to the size of the distal opening 1730 of the catheter 1705 as the capturing basket is pulled through the inflatable balloon catheter 1710. The proximal end of the inflatable balloon catheter 1705 connects to the distal opening 1730 of the catheter 1705. The objects such as the capturing basket and emboli, that traverse the inflatable balloon catheter 1710, enter the catheter 1705 through the distal opening 1730 of the catheter 1705.

The inflatable balloon catheter 1715 may have various shapes other than the funnel shape shown in FIG. 17A. In various embodiments, the inflatable balloon catheter 1715 has a disc shape or a cylindrical shape. The shape of the inflatable balloon catheter may be any shape that facilitates the retrieval of the capturing basket.

Figure 17B:
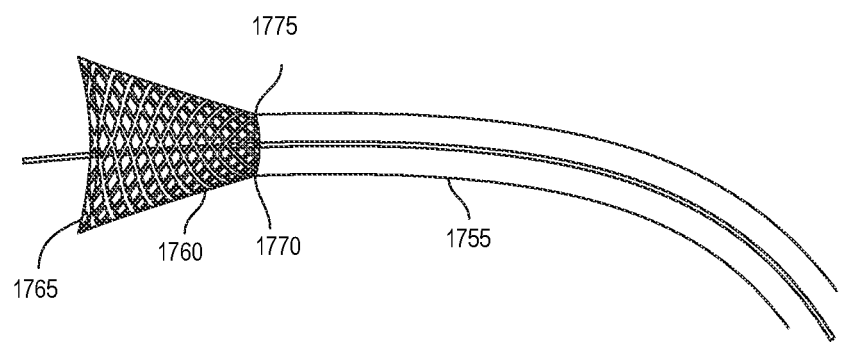
FIG. 17B is an illustration of an embodiment of the embolus retrieving apparatus that includes an inflatable balloon catheter with a grid.

Referring to FIG. 17B, FIG. 17B is an illustration 1750 of an embodiment of the embolus retrieving apparatus that includes an inflatable balloon catheter 1760 that has a grid. The inflatable balloon catheter 1760 has a similar shape to the inflatable balloon catheter 1710 shown in FIG. 17A. As shown in FIG. 17B, the inflatable balloon catheter 1760 has a grid structure. The grid structure in the inflatable balloon catheter 1760 may allow blood to pass through the inflatable balloon catheter 1760 while stopping larger objects such as the capturing basket or emboli.

The blood-permeable grid structure of the inflatable balloon catheter 1760 allows blood to flow through a blood vessel while the inflatable balloon catheter 1760 expands to block the blood vessel. Objects that are larger than the grid in the inflatable balloon catheter 1760 may be blocked from passing through the inflatable balloon catheter 1760.

Like the inflatable balloon catheter 1710 shown in FIG. 17A, the inflatable balloon catheter 1760 has a distal opening 1765 and a proximal opening 1770. The proximal opening 1770 of the inflatable balloon catheter 1760 leads directly into the distal opening 1775 of the catheter 1755. Emboli that are trapped within the capturing basket may be pulled into the inflatable balloon catheter 1760 by a guidewire.

Figure 18A:
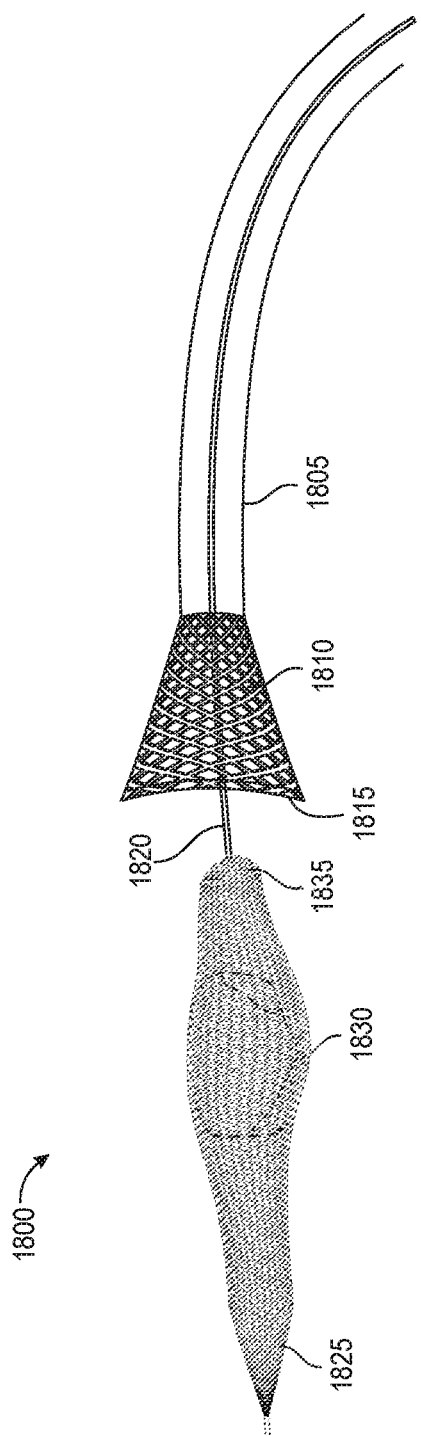
FIG. 18A is an illustration of an embodiment of the embolus retrieving apparatus that includes an inflatable balloon catheter with a grid.

Referring to FIG. 18A, FIG. 18A is an illustration 1800 of an embodiment of the embolus retrieving apparatus that includes an inflatable balloon catheter 1810 that has a grid. As shown in FIG. 18A, the capturing basket 1825 has surrounded an embolus 1830. The capturing basket 1825 with embolus 1830 inside the capturing basket 1825 attached to a distal end of a guidewire 1820. The guidewire 1820 runs through the catheter 1805 and inflatable balloon catheter 1810.

As shown in FIG. 18A, the profile of the embolus 1830 is larger than the diameter of the catheter 1805. Therefore, the embolus 1830, which is inside the capturing basket 1825, has to be distorted to fit into the catheter 1805. The embolus 1830 may be distorted and shaped to fit into the catheter 1805 in various ways. In one implementation of distorting the embolus 1830, the embolus 1830 may be sheared by reducing the size of the proximal opening 1835 of the capturing basket 1825 when the proximal opening 1835 is around the embolus 1830. In another implementation, the embolus 1830 may be sheared with retractable sharp edges on the inner surface of the catheter 1805. In another implementation, the embolus 1830 may be distorted in shape by forcing the embolus 1830, while the embolus 1830 is trapped in the capturing basket 1825, into the catheter 1805. In another implementation, shown in FIG. 18B, the embolus 1830 is squeezed into the catheter 1805 by pulling the embolus 1830 through the inflatable balloon catheter 1810.

Figure 18B:
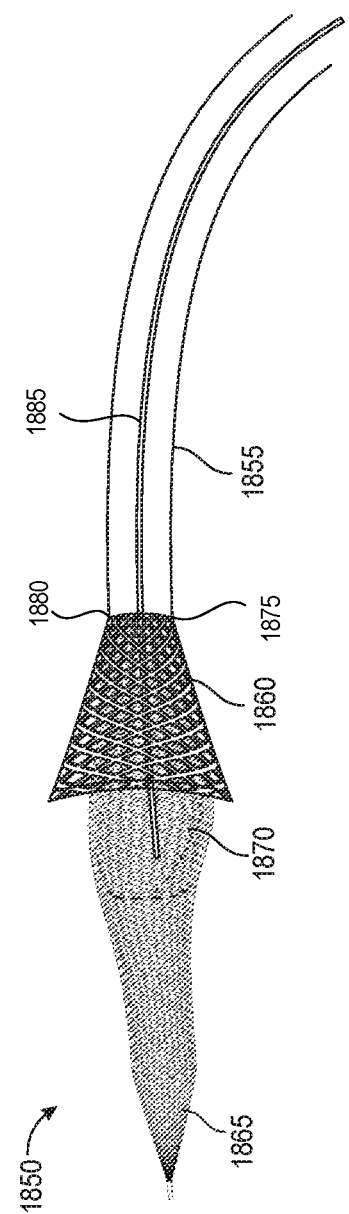
FIG. 18B is an illustration of an embodiment of the embolus retrieving apparatus that includes an inflatable balloon catheter with a grid.

Referring to FIG. 18B, is an illustration 1850 of an embodiment of the embolus retrieving apparatus that includes an inflatable balloon catheter 1860 that has a grid. The inflatable balloon catheter 1860 has retrieved a capturing basket 1865 that has surrounded an embolus 1870. As the embolus 1870 and capturing basket 1865 are retrieved, blood may continue to flow through the grid of the inflatable balloon catheter 1860.

The guidewire 1885 pulls the capturing basket 1870 through the inflatable balloon catheter 1860 to the proximal opening 1875 of the inflatable balloon catheter 1860. The proximal opening 1875 is directly attached to the distal opening 1880 of the catheter 1855. As the capturing basket 1865, which has surrounded an embolus 1870, is pulled through the inflatable balloon catheter, the capturing basket 1870 is squeezed by the gradually narrowing diameter of the funnel shape of the inflatable balloon catheter 1860. The funnel shape of the inflatable balloon catheter 1860 distorts the embolus 1870 as the embolus 1870, within the capturing basket 1865, is pulled through the inflatable balloon catheter 1860. As opposed to pulling the embolus 1870 directly into the catheter 1855, as shown in FIG. 10, the gradual squeezing of the embolus 1870 may lower the amount of energy required to distort the embolus 1870 so that the embolus 1870 will fit within the catheter 1855.

After the capturing basket 1865 and embolus 1870 are retrieved by the catheter 1855, the inflatable balloon catheter 1860 may be deflated in order to be extracted from the blood vessel. The inflatable balloon catheter 1860 may be placed in the blood vessel and extracted from the blood vessel while the inflatable balloon catheter 1860 is in a deflated state. The catheter 1855 may be pulled to an extraction location by the guidewire 1885.

The embodiments of the embolus retrieving apparatus described herein may be made in many variations. Every variation of the apparatus, including all variations of the capturing basket and all variations of the catheter and all variations of the funnel shaped balloon are intended to be included in the scope of this disclosure. The terminology used to describe the apparatus is intended to aid in the understanding of the many variations rather than to restrict the many variations. The scope of the disclosed subject matter should instead be defined in accordance with the appended claims.

The invention claimed is:

1. A clot retrieval device comprising:
   a capturing basket having an opening at a proximal end;
   a delivery catheter;
   wherein the capturing basket is deployable downstream from a clot in a blood vessel;
   wherein the capturing basket is configured to surround a portion of the clot and the opening in the proximal end of the capturing basket is configured to reduce in size such that the capturing basket conforms around the portion of the clot;
   wherein the capturing basket is configured to be retrieved by a distal opening of the delivery catheter after the capturing basket conforms around the portion of the clot;
   wherein the capturing basket has spaced pores that increase in size from a distal end of the capturing basket to the proximal end of the capturing basket;
   wherein the distal opening of the delivery catheter has one or more extrusions extending from an inner surface of the delivery catheter;
   wherein the one or more extrusions have sharp edges;
   wherein the one or more extrusions are retractable; and
   wherein the one or more extrusions are configured to shear the clot when the capturing basket is retrieved by the distal end of the delivery catheter.

2. The clot retrieval device of claim 1,
   wherein the capturing basket comprises braided wire and the spaced pores are formed from spaces between the braided wire; and
   wherein a distal end of the capturing basket is made of a soft material such that the distal end of the capturing basket is deformable upon contact with an interior wall of the blood vessel.

3. The clot retrieval device of claim 1, wherein the capturing basket comprises a tube that is cut with a laser and the spaced pores are created by the laser.

4. The clot retrieval device of claim 3, wherein the capturing basket comprises a combination of braided wire and a tube that is cut with a laser.

5. The clot retrieval device of claim 4, wherein a portion of the combination of braided wire and the tube that is cut with a laser has a textured surface.

6. The clot retrieval device of claim 4, wherein the braided wire comprises Nitinol.

7. The clot retrieval device of claim 6, wherein the capturing basket includes radiopaque material; and
wherein the radiopaque material is positioned to reveal the clot under fluoroscopy when the capturing basket conforms to the portion of the clot.

8. The clot retrieval device of claim 1, wherein the capturing basket is configured to be delivered by the delivery catheter from an upstream direction in the blood vessel prior to being retrieved by the delivery catheter;
wherein the delivery catheter has one or more slits at the distal opening of the delivery catheter; and
wherein the distal opening of the delivery catheter is configured to increase in size to retrieve the capturing basket.

9. A clot retrieval device comprising:
a capturing basket having an opening at a proximal end;
a delivery catheter configured to deliver the capturing basket from a distal end of the delivery catheter;
wherein the capturing basket has spaced pores formed from spaces between a braided wire that increase in size from a distal end of the capturing basket to the proximal end of the capturing basket;
wherein the capturing basket is configured to surround a portion of the clot and the opening in the proximal end of the capturing basket is configured to reduce in size such that the capturing basket conforms around the portion of the clot;
wherein the capturing basket is configured to be retrieved by the distal opening of the delivery catheter after the capturing basket conforms around the portion of the clot;
wherein the distal opening of the delivery catheter has one or more extrusions extending from an inner surface of the delivery catheter;
wherein the one or more extrusions have sharp edges;
wherein the one or more extrusions are retractable; and
wherein the one or more extrusions are configured to shear the clot when the capturing basket is retrieved by the distal end of the delivery catheter.

10. The clot retrieval device of claim 9:
wherein the delivery catheter has one or more slits at the distal opening of the delivery catheter; and
wherein the distal opening of the delivery catheter is configured to increase in size to retrieve the capturing basket.

11. The clot retrieval device of claim 10, further comprising:
a balloon catheter located near the distal opening of the delivery catheter that has a funnel shape when inflated; and
wherein the balloon catheter has pores that, when the balloon catheter is inflated, allow blood to flow through the balloon catheter and prevent large blood clots from flowing through the balloon catheter.

12. The clot retrieval device of claim 9, wherein a proximal end of the delivery catheter is configured to be aspirated to aid in the retrieval of the capturing basket into the distal end of the delivery catheter.

* * * * *